(12) United States Patent
Lees

(10) Patent No.: US 6,309,646 B1
(45) Date of Patent: Oct. 30, 2001

(54) PROTEIN-POLYSACCHARIDE CONJUGATE VACCINES AND OTHER IMMUNOLOGICAL REAGENTS PREPARED USING HOMOBIFUNCTIONAL AND HETEROBIFUNCTIONAL VINYLSULFONES, AND PROCESSES FOR PREPARING THE CONJUGATES

(75) Inventor: Andrew Lees, Silver Spring, MD (US)

(73) Assignee: The Henry M. Jackson Foundation for the Advancement of Military Medicine, Rockville, MD (US)

( * ) Notice: Subject to any disclaimer, the term of this patent is extended or adjusted under 35 U.S.C. 154(b) by 0 days.

(21) Appl. No.: 08/852,733

(22) Filed: May 7, 1997

Related U.S. Application Data

(60) Provisional application No. 60/017,103, filed on May 9, 1996.

(51) Int. Cl.[7] ............................ A61K 47/36; A61K 47/42
(52) U.S. Cl. .................................. 424/195.11; 424/194.1; 424/193.1; 514/54; 514/23; 514/8; 530/402; 436/528; 436/529; 436/530; 436/532; 436/822; 436/823; 436/828
(58) Field of Search ............................ 530/402; 436/528, 436/529, 530, 532, 822, 823, 828; 424/195.11, 194.1, 193.1; 514/8, 54, 23

(56) References Cited

U.S. PATENT DOCUMENTS

| | | |
|---|---|---|
| 3,788,948 | 1/1974 | Kagedal et al. . |
| 4,057,685 | 11/1977 | McIntire .................................. 536/18 |
| 4,175,073 | 11/1979 | Carlsson et al. . |
| 4,185,090 | 1/1980 | McIntire . |
| 4,275,000 | 6/1981 | Ross . |
| 4,328,311 | 5/1982 | Rowley et al. . |
| 4,356,170 | 10/1982 | Jennings et al. . |
| 4,451,446 | 5/1984 | Vandevelde et al. . |
| 4,459,286 | 7/1984 | Hilleman et al. . |
| 4,493,795 | 1/1985 | Nestor et al. . |
| 4,695,624 | 9/1987 | Marburg et al. . |
| 4,910,135 | 3/1990 | Tischer et al. . |
| 4,931,392 | 6/1990 | Rehner et al. . |
| 5,153,312 | 10/1992 | Porro ..................................... 530/405 |
| 5,177,059 | 1/1993 | Handley et al. . |
| 5,204,098 | 4/1993 | Szu et al. . |
| 5,306,492 | 4/1994 | Porro ..................................... 424/88 |
| 5,425,946 | 6/1995 | Tai et al. . |
| 5,543,332 * | 8/1996 | Lihme et al. ......................... 436/528 |
| 5,651,971 | 7/1997 | Lees . |
| 5,693,326 | 12/1997 | Lees . |

FOREIGN PATENT DOCUMENTS

| | | |
|---|---|---|
| 1815332 | 7/1969 | (DE) . |
| 186576 | 7/1986 | (EP) . |
| 0428486 | 5/1991 | (EP) . |
| WO93/15760 | 8/1983 | (WO) . |
| WO93/1498 | 1/1993 | (WO) . |
| WO94/25060 | 11/1993 | (WO) . |
| WO/95/8348 | 3/1995 | (WO) . |

OTHER PUBLICATIONS

Ellman, "Tissue Sulfhydryl Groups," Archives of Biochemistry and Biophysics, vol. 82, pp. 70–77 (1959).

Brunswick et al., "Picogram Quantities of Anti–lg Antibodies Coupled to Dextran Induce B Cell Proliferation," The Journal of Immunology, vol. 140, No. 10, 1968, pp. 3364–3372.

Kagedal et al., "Binding of Covalent Proteins to Polysaccharides by Cyanogen Bromide and Organic Cyanates. I. Preparation of Soluble Glycine–, Insulin– and Ampicillin–dextran," Acta Chemical Scandinavica, vol. 25, No. 5, 1971, pp. 1855–1859.

Porath, "General Methods and Coupling Procedures," Affinity Techniques, vol. 34, 1974, pp. 13–31.

Inman, "Thymus–Independent Antigens: The Preparation of Covalent, Hapten–Ficoll Conjugates," Journal of Immunology, vol. 114, No. 2, Part 1, Feb. 1975, pp. 704–709.

Köhler et al., "Continuous cultures of fused cells secreting antibody of predefined specificity," Nature, vol. 256, 1975, pp. 495–497.

Porath et al., "Immobilization of Enzymes to Agar, Agarose, and Sephadex Supports," Methods In Enzymology, vol. 44, Immobilized Enzymes, 1976, pp. 19–45.

Wakselman et al., "1–Cyano–4–dimethylamino–pyridinium Salts: New Water–soluble Reagents for the Cyanylation of Protein Sulphydryl Groups," J.C.S. Chem. Comm., 1976, pp. 21–22.

(List continued on next page.)

Primary Examiner—T. D. Wessendorf

(57) ABSTRACT

A method is disclosed for producing a soluble conjugate vaccine, and preferably protein/polysaccharide conjugates. In this process, the polysaccharide is reacted with a reagent so as to provide a functional group on the polysaccharide molecule. Once the functional group is in place, the polysaccharide is reacted with a homobifunctional or heterobifunctional vinylsulfone to produce a vinylsulfone derivatized polysaccharide. Thereafter, the vinylsulfone derivatized polysaccharide is reacted with a protein to produce the conjugate. If desired, the protein may be derivatized with a functional group prior to the conjugation reaction step. In an alternative embodiment, the protein may be functionalized with a reactive group and then derivatized with the vinylsulfone group to produce a vinylsulfone derivatized protein. This protein may then be reacted with a polysaccharide to produce the conjugate. Optionally, the polysaccharide may be functionalized with a reactive group prior to the conjugation reaction. As another alternative, the polysaccharide may be derivatized directly with a pendant vinylsulfone of the crosslinking agent. The vinylsulfone derivatized polysaccharide may then be coupled to the protein (which may or may not be functionalized). In a similar manner, the protein may be derivatized directly with a pendant vinylsulfone of the crosslinking agent and then coupled to a polysaccharide molecule (which may or may not be functionalized).

2 Claims, 12 Drawing Sheets

OTHER PUBLICATIONS

Wong et al., "Standardization and control of meningococcal vaccines, group A and group C polysaccharides," Journal of Biological Standardization, vol. 5, 1977, pp. 197–215.

Erlanger, "The Preparation of Antigenic Hapten–Carrier Conjugates: A Survey," Methods in Enzymology, vol. 70, Immunochemical Techniques, 1980, pp. 85–104.

Nolan et al., "Evaluation of a New Assay for Vi Antibody in Chronic Carriers of *Salmonella typhi*," Journal of Clinical Microbiology, vol. 12, No. 1, Jul. 1980, pp. 22–26.

Schneerson et al., "Preparation, Characterization, and Immunogenicity of *Haemophilus influenza* Type b Polysaccharide–Protein Conjugates," The Journal of Experimental Medicine, vol. 152, No. 1, 1980, pp. 361–376.

Kohn et al., "Procedures for the Analysis of Cyanogen Bromide–Activated Sepharose or Sephadex by Quantitative Determination of Cyanate Esters and Imidocarbonates," Analytical Biochem., vol. 115, 1981, pp. 375–382.

Kohn et al., "1–Cyano–4–dimethylamino pyridinium tetrafluoroborate as a cyanylating agent for the covalent attachment of ligand to polysaccharide resins," FEBS Letters, vol. 154, No. 1, 1983, pp. 209–210.

Chu et al., "Further Studies on the Immunogenicity of *Haemophilus influenza* Type b and Pneumococcal Type 6A Polysaccharide–Protein Conjugates," Infection and Immunity, Apr. 1983, pp. 245–256.

Wilchek et al., "Affinity Chromatography," Methods in Enzymology, vol. 104, 1984, pp. 3–55.

McKenzie et al., "Cholera Toxin B Subunit as a Carrier Protein to Stimulate a Mucosal Immune Response," Journal of Immunology, vol. 133, No. 4, 1984, pp. 1818–1824.

Robbins et al., "Reexamination of the Protective Role of the Capsular Polysaccharide (Vi antigen) of *Salmonella typhi*," Journal of Infectious Diseases, vol. 150, No. 3, Sep. 1984, pp. 436–449.

Kohn et al., "The Use of Cyanogen Bromide and Other Novel Cyanylating Agents for the Activation of Polysaccharide Resins," Applied Biochemistry and Biotechnology, vol. 9, 1984, pp. 285–305.

Marburg et al., "Bimolecular Chemistry of Macromolecules: Synthesis of Bacterial Polysaccharide Conjugates with *Neisseria meningitidis* Membrane Protein," J. Am. Chem. Soc., vol. 108, 1986, pp. 5282–5287.

Tacket et al., "Safety and Immunologenicity to Two *Salmonella typhi* Vi Capsular Polysaccharide Vaccines," Journal of Infectious Diseases, vol. 154, No. 2, Aug. 1986, pp. 342–345.

Ishii et al., "Effects of the State of the Succinimido–Ring on the Fluorescence and Structural Properties of Pyrene Maleimide–Labeled αα–Tropomyosin," Biophysical Journal, vol. 50, No. 1, Jul. 1986, pp. 75–80.

Wileman et al., "Soluble asparaginase–dextran conjugates show increased circulatory persistence and lowered antigen reactivity," J. Pharm. Pharmacol., vol. 38, 1986, pp. 264–271.

Letters to the Editor, Re.: "Trinitrophenyl–protein conjugates are more complex than it is currently thought," Journal of Immunological Methods, vol. 86, 1986, pp. 155–156.

Szu et al., "Vi Capsular Polysaccharide–Protein Conjugates for Prevention of Typhoid Fever," Journal of Experimental Medicine, vol. 166, Nov. 1987, pp. 1510–1524.

Masri et al., "Protein Reactions with Methyl and Ethyl Vinyl Sulfones," Journal of Protein Chemistry, vol. 7, No. 1, 1988, pp. 49–54.

Monsigny et al., "Colorimetric Determination of Neutral Sugars by a Resorcinol Sulfuric Acid Micromethod," Analytical Biochemistry, vol. 175, 1988, pp. 525–530.

Dick, Jr., et al., "Glycoconjugates of Bacterial Carbohydrate Antigens," Conjugate Vaccines, vol. 10, 1989, pp. 48–114.

Andersson et al., "Binding of Epidermal Growth Factor–Dextran Conjugates to Cultured Glioma Cells," Int. J. Cancer, vol. 47, 1991, pp. 439–444.

Messner et al., "Artificial Antigens, Synthetic Carbohydrate Haptens Immobilized on Crystalline Bacterial Surface Layer Glycoproteins," Carbohydrate Research, vol. 223, 1992, pp. 175–184.

Brinkley, "A Brief Survey of Methods for Preparing Protein Conjugates with Dyes, Haptens, and Cross–Linking Reagents," Bioconjugate Chem., vol. 3, 1992, pp. 2–13.

Carpenter et al., "Preparation of Heparin–Glyceryl Controlled–Pore Glass Affinity Media for the Separation of α– and β–lipoproteins," Journal of Chromography, vol. 573, 1992, pp. 132–135.

Lees et al., "Enhanced immunogenicity of protein–dextran conjugates: I. Rapid stimulation of enhanced antibody responses to poorly immunogenic molecules," Vaccine, vol. 12, No. 13, 1994, pp. 1160–1166.

Pepper, "Some Alternative Coupling Chemistries for Affinity Chromatography," Molecular Biotechnology, vol. 2, 1994, pp. 157–178.

Romanowska et al, "Michael Additions for Syntheses of Neoglycoproteins," Methods of Enzymology, vol. 242, 1994, pp. 90–101.

Houen et al., "Conjugation to Preactivated Proteins Using Divinylsulfone and Iodoacetic Acid," Journal of Immunological Methods, vol. 181, 1995, pp. 187–200.

Lees et al., "Activation of Soluble Polysaccharides with 1–Cyano–4–Dimethylaminopyridinium Tetrafluoroborate for Use in Protein–Polysaccharide Conjugate Vaccines and Immunological Reagents," Vaccine, vol. 14, No. 3, 1996, pp. 190–198.

Morpurgo et al., "Preparation and Characterization of Poly-(ethylene glycol) Vinyl Sulfone," Bioconjugate Chemistry, vol. 7, 1996, pp. 363–368.

Hermanson, "Homobifunctional Cross–Linkers," Bioconjugate Techniques, 1996, pp. 187–227.

"CDAP: Monoclonal Coupler", Research Organics, Inc.

"Group Four—Sulfyhdyrl–Selective Pegs," "Group Five—Heterofunctional Pegs," Shearwater Polymers, Inc. p. 30 and p. 35.

"Brief Review of Peg Applications," Shearwater Polymers, Inc., pp. 42–43.

"Homobifunctional Maleimides," Molecular BioScience, pp. 263–267.

* cited by examiner

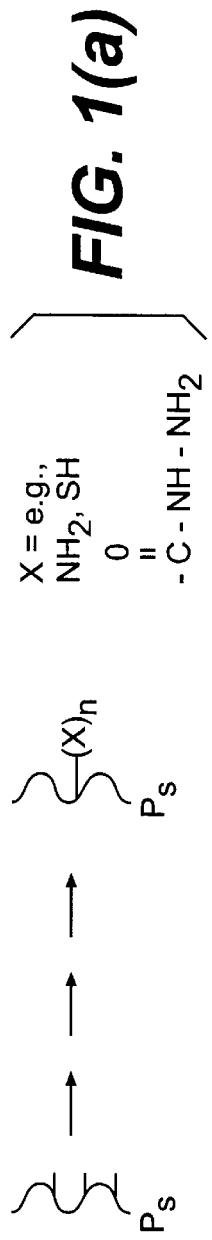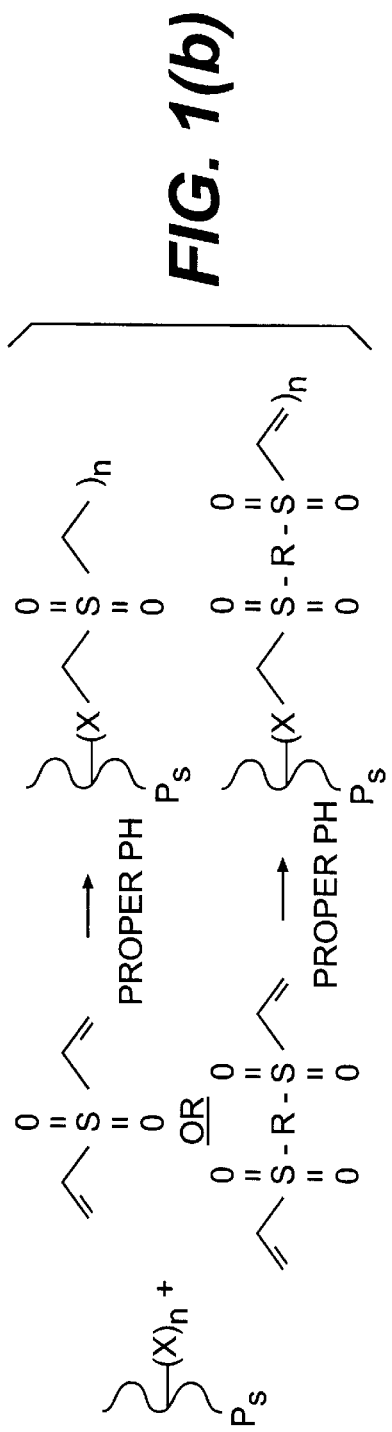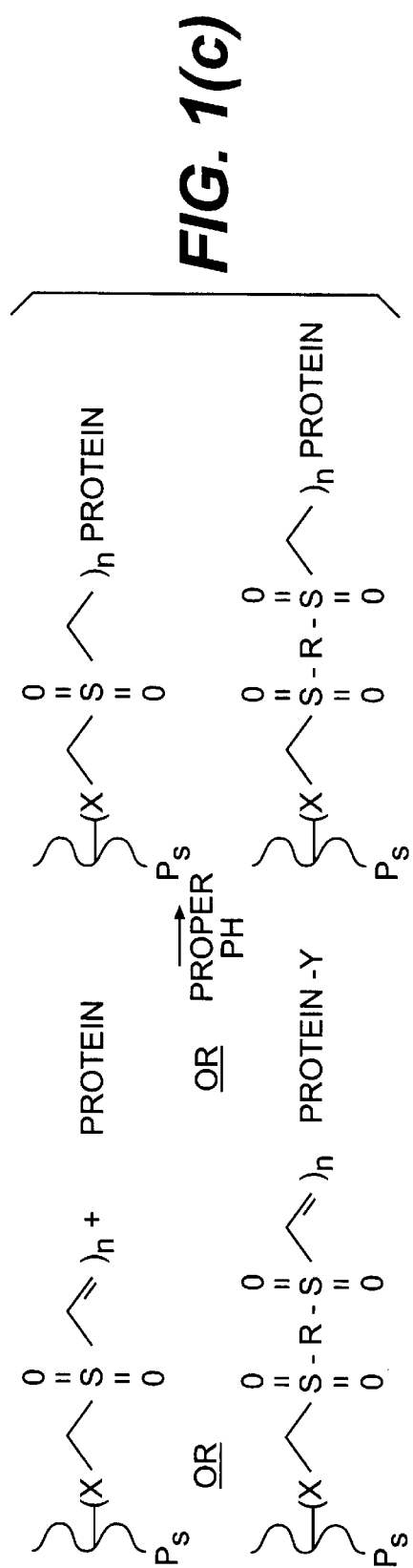

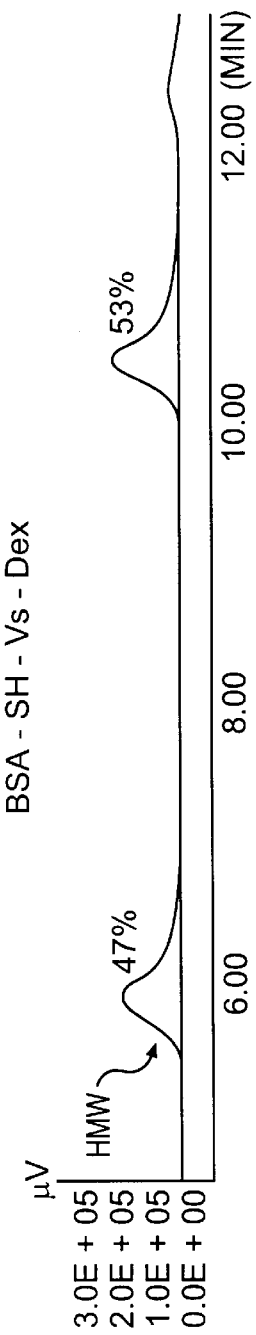
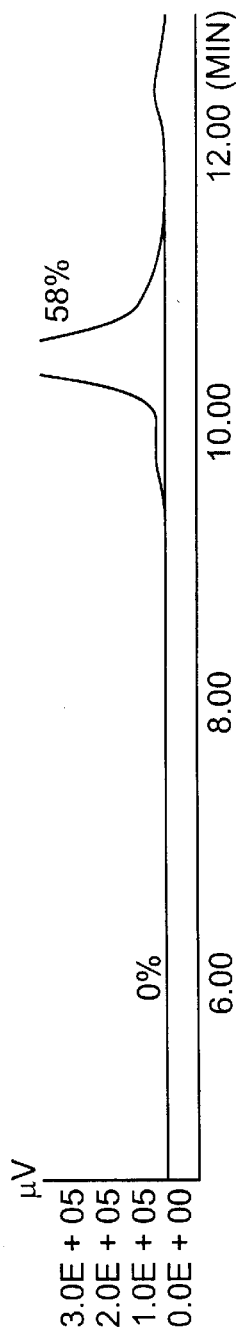
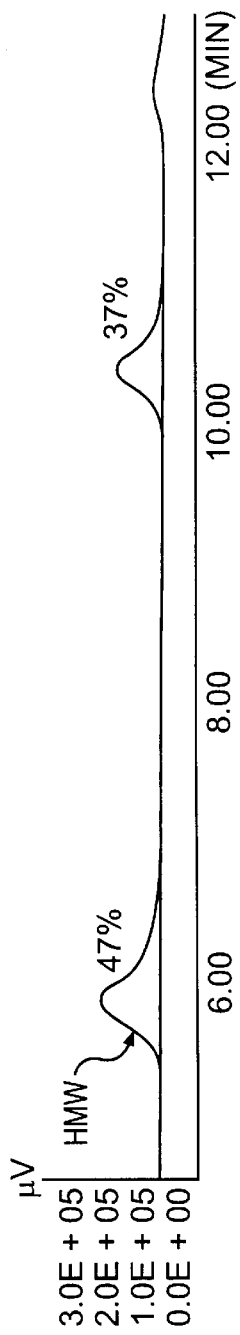
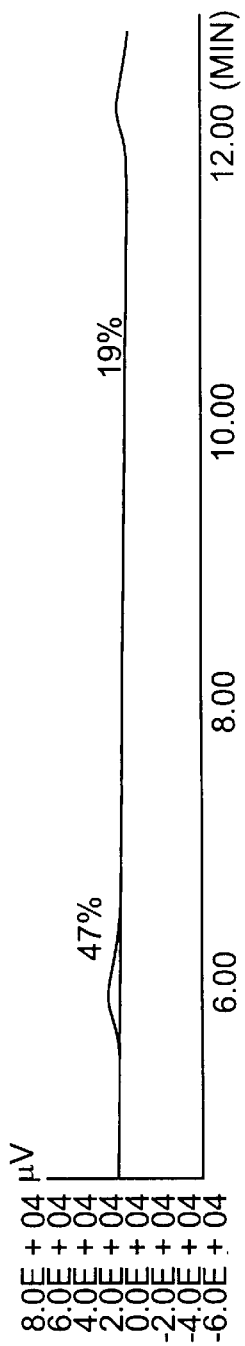
FIG. 4(a)
FIG. 4(b)
FIG. 4(c)
FIG. 4(d)

PROTEIN + SPDP ⟶ PROTEIN - (SH)$_n$
FIG. 7(a)
$P_s$ ⟶ $P_s$ - NH$_2$
CDAD
HEXANEDIAMINE
FIG. 7(b)
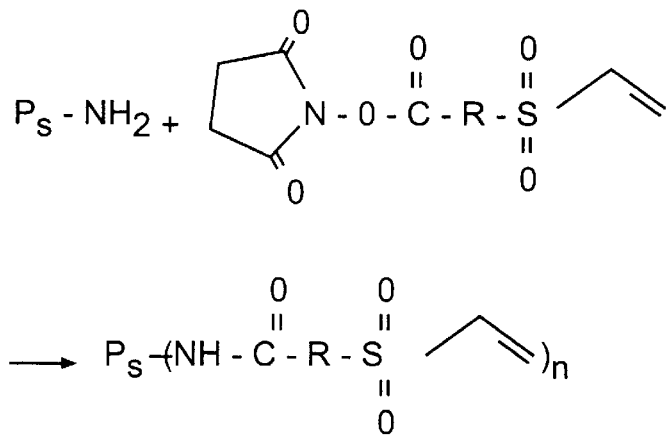
FIG. 7(c)
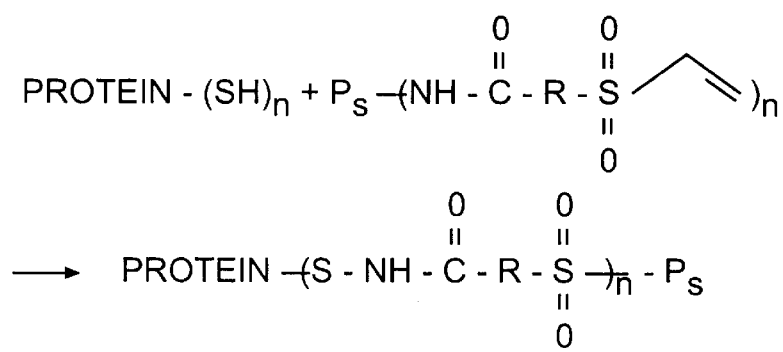
FIG. 7(d)

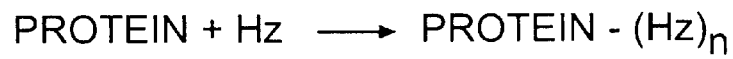
FIG. 8(a)
FIG. 8(b)
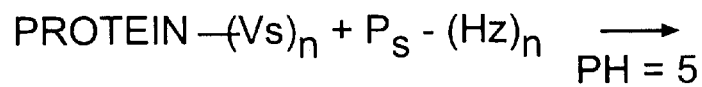
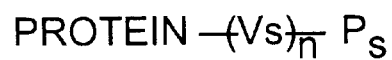
FIG. 8(c)

PROTEIN-POLYSACCHARIDE CONJUGATE VACCINES AND OTHER IMMUNOLOGICAL REAGENTS PREPARED USING HOMOBIFUNCTIONAL AND HETEROBIFUNCTIONAL VINYLSULFONES, AND PROCESSES FOR PREPARING THE CONJUGATES

RELATED APPLICATION DATA

This application claims priority benefits under 35 U.S.C. §119 based on U.S. Provisional Patent Application No. 60/017,103, filed May 9, 1996, which application is entirely incorporated herein by reference.

BACKGROUND OF THE INVENTION

Vaccines have been very effective in protecting people from a wide variety of diseases, whether caused by viruses, bacteria, or fungi. The ability of vaccines to induce specific protection to such a wide range of pathogenic organisms results from their ability to stimulate specific humoral antibody responses, as well as cell-mediated responses. This invention relates to such vaccines, and particularly to a process for making conjugates, such as protein/polysaccharide conjugates, that are used in the preparation of vaccines and other valuable immunological reagents. The invention further relates to the vaccines and immunological reagents that are produced from the conjugates made in accordance with the invention.

Certain agents can stimulate an immune response with minimal chemical modifications, such as, for example, tetanus toxoid, which is immunogenic even in the absence of adjuvant. Other important agents are either non-immunogenic or poorly immunogenic, but they can be converted into immunogenic molecules or constructs, in which form they can induce vigorous immune responses. For example, most polysaccharides are poorly immunogenic. After they are coupled to proteins, however, the resulting construct becomes immunogenic. The conjugation of proteins to polysaccharides converts the polysaccharide from a weakly immunogenic T-cell independent antigen to a T-cell dependent antigen that recruits T-cell help, and thus stimulates heightened immune responses. Note the discussion by J. M. Cruse, et al. (Editors.), *Conjugate Vaccines*, Karger, Basel, (1989); and R. W. Ellis, et al. (Editors), *Development and Clinical Uses of Haemophilus B Conjugate Vaccines*, Marcel Dekker, New York (1994). These books are entirely incorporated herein by reference.

Conjugation of a protein and a polysaccharide may provide other advantageous results. For example, Applicant has found that a protein/polysaccharide conjugate enhances the antibody response not only to the polysaccharide component, but also to the protein component. This effect is described, for example, in the dual conjugate patent application of Mond and Lees, U.S. patent application Ser. No. 08/402,565 (filed Mar. 13, 1995, now U.S Pat. No. 5,585,100); application Ser. No. 08/444,727 (filed May 19, 1995, now abandoned); and application Ser. No. 08/468,060 (filed Jun. 6, 1995, now abandoned). These patent applications each are entirely incorporated herein by reference. This effect also is described in A. Lees, et al., "Enhanced Immunogenicity of Protein-Dextran Conjugates: I. Rapid Stimulation of Enhanced Antibody Responses to Poorly Immunogenic Molecules," *Vaccine*, Vol. 12, No. 13 (1994), pp. 1160–1166. This article is entirely incorporated herein by reference.

Techniques have been developed to facilitate coupling of proteins and polysaccharides. Note W. E. Dick, et al., "Glyconjugates of Bacterial Carbohydrate Antigens: A Survey and Consideration of Design and Preparation Factors," *Conjugate Vaccines* (Eds. Cruse, et al.,), Karger, Basel, 1989, beginning at page 48. This excerpt also is entirely incorporated herein by reference. Many techniques for activation of carbohydrates, however, are not suitable for use in aqueous media because the activating or functional reagents are not stable in water. For example, the use of N,N'-carbonyldiimidazole is described in Marburg et al., U.S. Pat. No. 4,695,624 (which patent is entirely incorporated herein by reference). This reagent must be used in organic media.

For use in aqueous media, applicant has developed the use of 1-cyano-4-(dimethylamino)-pyridinium tetrafluoroborate, also called "CDAP" in this patent application, to activate polysaccharides. These activated polysaccharides may be directly or indirectly coupled to proteins. The use of CDAP is described in the following U.S. patent applications of Andrew Lees: U.S. patent application Ser. No. 08/124,491 (filed Sep. 22, 1993, now abandoned), U.S. patent application Ser. No. 08/408,717 (filed Mar. 22, 1995), and U.S. patent application Ser. No. 08/482,666 (filed Jun. 7, 1995). These U.S. patent applications each are entirely incorporated herein by reference. The use of CDAP also is described in Lees, et al., "Activation of Soluble Polysaccharides with 1-Cyano-4-Dimethylamino Pyridinium Tetrafluoroborate For Use in Protein-Polysaccharide Conjugate Vaccines and Immunological Reagents," *Vaccine*, Vol. 14, No. 3 (1996), pp. 190–198. This article also is entirely incorporated herein by reference.

Some polysaccharides have few or cryptic hydroxyls. Thus, these polysaccharides are not suitable for direct derivatization with vinylsulfone, nor for activation by other common methods, such as CNBr activation. Examples of such polysaccharides are Vi antigen and *Neisseria meningiditis* polysaccharide type C ("Neisseria PsC"). Additionally, some polysaccharides are pH sensitive. Thus, they are unsuitable for direct derivatization with vinylsulfone. Examples of such polysaccharides are *Haemophilus influenzae* type B ("PRP"), and Vi. Thus, the ability to perform the entire derivatization process at a lower pH may be important for derivatizing certain polysaccharides.

Often, however, the process of coupling a protein and a polysaccharide may lead to undesirable effects. In some cases, direct coupling can place the protein and polysaccharide in very close proximity to one another and encourage the formation of excessive crosslinks between the protein and the polysaccharide. Under the extreme of such conditions, the resultant material can become very thick (e.g., in a gelled state). Such a material would not be useful as a vaccine formulation.

Over-crosslinking also can result in decreased immunogenicity of the protein and polysaccharide components. In addition, the crosslinking process can result in the introduction of foreign epitopes into the conjugate or can otherwise be detrimental to production of a useful vaccine. The introduction of excessive crosslinks exacerbates this problem.

To limit the probability of excess crosslinking between the protein and polysaccharide, a spacer may be provided between the protein and polysaccharide. The spacer helps maintain physical separation between the protein and polysaccharide molecules, and it can be used to limit the number of crosslinks between the protein and polysaccharide. As an additional advantage, spacers also can be used to control the structure of the resultant conjugate. If a conjugate does not have the correct structure, problems can result that can adversely affect the immunogenicity of the conjugate material. The speed of coupling, either too fast or too slow, also can affect the overall yield, structure, and immunogenicity of the resulting conjugate product. Note Schneerson et al., *Journal of Experimental Medicine,* Vol. 152, beginning at pg. 361 (1980). This article is entirely incorporated herein by reference. Spacers help regulate the kinetics of the conjugation reaction.

In view of the potential advantages of using spacers, it is desirable to provide a process where a protein is coupled to a polysaccharide via a spacer. In this coupling procedure, spacers are used in the chemical reaction that is needed to join the protein with the polysaccharide. Spacers facilitate this chemical reaction by providing a functional group on one of the molecules that will react with a group present on the other molecule. Either the polysaccharide molecule or the protein molecule may be derivatized with the spacer molecule including the reactive functional group. If necessary, the other molecule also may be separately derivatized with a reactive functional group (e.g., a thiol, hydrazide, or amine) that will facilitate reaction with the spacer during conjugation.

The possible use of homobifunctional vinylsulfones has been considered for certain conjugation reaction processes. One member of this group is divinylsulfone, which has the following structure:

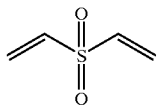

Divinylsulfone has been used to crosslink proteins and to derivatize proteins with haptens. Note, for example, "Conjugation to Preactivated Proteins Using Divinylsulfone and Iodoacetic Acid," by Gunnar Houen, et al., *Journal of Immunological Methods,* Vol. 181 (1995), pp. 187–200. This article is entirely incorporated herein by reference. The Houen article describes the coupling of a small protein (10 kDa) derivatized with divinylsulfone (DVS) to the lysines of a 45 kDa protein. Only low levels of protein coupling were observed. This article also describes the coupling of small haptens and peptides to highly derivatized DVS-protein. A large excess of the hapten was used in the described process. In this method, no effort was made to limit the degree of derivatization with divinylsulfone or to maintain the integrity of the protein. Indeed, in Houen, the goal was maximum derivatization of the protein.

Other researchers have described the use of divinylsulfone to couple proteins and haptens to solid phase gels with the purpose of obtaining affinity chromatography gels. See Porath, "General Methods and Coupling Procedures," *Methods in Enzymology,* Vol. 34 (1974), pgs. 13–30, and Porath et al,. "Immobilization of Enzymes to Agar, Agarose, and Sephadex Supports," *Methods in Enzymology,* Vol. 44 (1976), pgs. 19–45. These Porath documents also are entirely incorporated herein by reference. Note also, S. Pepper, "Some Alternative Coupling Chemistries for Affinity Chromatography," *Molecular Biotechnology,* Vol. 2 (1994), pp. 157–178. This article is entirely incorporated herein by reference. Problems with over-crosslinking and poor yield are described by Porath. Furthermore, these described methods for derivatizing with divinylsulfone required prolonged exposure to a high pH (pH 11). The combination of the multiplicity of the polysaccharide hydroxyl groups and the harsh reaction conditions promotes or induces over-crosslinking and aggregation of the polysaccharide. Such reaction conditions would be unsuitable for preparing soluble protein-polysaccharide conjugates.

The use of vinylsulfone derivatized polyethylene glycol ("PEG") to react with protein thiols and amines has been described by other researchers. See, for example, Morpurgo, et al., "Preparation and Characterization of Polyethylene Glycol Vinylsulfone," *Bioconjugate Chemistry,* Vol. 7 (1996), beginning at page 363 (which article is entirely incorporated herein by reference). The purpose of functionalizing with PEG, however, is to reduce the immunogenicity of the protein.

In addition to all of the above-noted problems in the reaction processes using divinylsulfone, other problems exist in using this material. In general, homobifunctional reagents, including divinylsulfone, have been found to produce a broad range of poorly defined conjugates. Note the discussion in G. T. Hermanson, *Bioconjugate Techniques,* Academic Press, San Diego, Calif., (1996), pg. 187. The entire *Bioconjugate Techniques* book is incorporated herein by reference.

In spite of these problems in using divinylsulfone, however, certain advantages exist for using this material. Divinylsulfone is a more universal linking reagent because it reacts with more nucleophiles as compared to iodoacetamides or maleimides. Other advantages of divinylsulfone relate to its availability, stability, water solubility, and cost. As compared to some agents used to derivatize proteins and/or polysaccharides, divinylsulfone is much less expensive and more readily available.

SUMMARY OF THE INVENTION

It is an object of this invention to provide methods for producing conjugates that avoid the problems and disadvantages described above. It is a further object of this invention to provide vaccines and other immunological reagents that are produced from these conjugates.

In a first step of one method according to the invention, a polysaccharide is reacted with a homobifunctional vinylsulfone reagent or a heterobifunctional vinylsulfone reagent to produce a vinylsulfone derivatized polysaccharide ("Ps-Vs"). The polysaccharide first may be derivatized in one or more steps in order to facilitate the reaction with the vinylsulfone reagent. In a second step, a protein, peptide, or hapten is reacted with the Ps-Vs under appropriate conditions to join it to the polysaccharide to produce the conjugate. In order to facilitate this coupling, the protein, peptide, or hapten may be modified by the addition of nucleophiles that are more reactive than the endogenous amines of the protein, peptide, or hapten. For example, a protein can be derivatized with thiol nucleophiles or hydrazide nucleophiles prior to the conjugation reaction.

The invention also relates to a conjugate material (e.g., a protein/polysaccharide conjugate) produced by the method described above. This conjugate may include a sulfone group (i.e., an

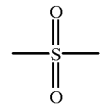

group) from the vinylsulfone in its structure as part of a spacer or crosslinking agent.

As an alternative method for producing a conjugate according to the invention, a protein, peptide, or hapten is reacted with a homobifunctional vinylsulfone reagent or a heterobifunctional vinylsulfone reagent to produce a vinylsulfone derivatized material (e.g., a "Protein-Vs"). The protein, peptide, or hapten first may be derivatized with other reactive groups in order to facilitate the reaction with the vinylsulfone reagent. A polysaccharide then is reacted with the vinylsulfone derivatized material under appropriate conditions, to join the protein, peptide, or hapten with the polysaccharide to produce the conjugate. In order to facilitate this coupling, the polysaccharide can be derivatized with a functional group (e.g., a nucleophilic group such as thiols, amines, or hydrazides) prior to the conjugation reaction.

The conjugates produced by this method also are a part of this invention. This conjugate may include a sulfone group from the vinylsulfone in its structure as part of a spacer or a crosslinking agent.

The above described methods in accordance with the invention allow for selective, limited, and mild derivatization of the protein, peptide, hapten, or polysaccharide as compared to the various derivatization methods using divinylsulfone described in the documents mentioned above.

Limited derivatization of the polysaccharide is accomplished by: (a) a multi-step derivatization process in which the polysaccharide is first derivatized with a limited number of reactive groups followed by reaction with an excess of a homobifunctional vinylsulfone reagent, or (b) derivatization of the polysaccharide with a limited number of nucleophiles followed by reaction with a heterobifunctional vinylsulfone reagent. Other means of derivatization may be available with respect to a particular polysaccharide, such as through coupling of an amine or hydrazide vinylsulfone reagent to oxidized polysaccharide, carbodiimide coupling, etc. Some polysaccharides contain many nucleophilic groups (e.g., hydroxyls or amines) that can be partially derivatized with the vinylsulfone reagent by controlling the reaction conditions.

Limited derivatization of the protein, peptide, or hapten component may be accomplished by: (a) directly reacting the homobifunctional vinylsulfone reagent or the heterobifunctional vinylsulfone reagent with the protein, peptide, or hapten, while controlling the reaction time, reagent concentrations, pH, etc; or (b) a multi-step derivatization process in which the protein, peptide, or hapten is first derivatized with a limited number of groups that are more reactive than the endogenous amines, followed by reaction with the homobifunctional vinylsulfone reagent or the heterobifunctional vinylsulfone reagent. Other means of limited derivatization may be available with respect to particular proteins, peptides, or haptens, e.g., coupling of an amine or hydrazide vinylsulfone reagent to oxidized protein, peptide, or hapten, or to carboxyls using carbodiimide.

The processes in accordance with the invention allow one to control the degree of derivatization of the polysaccharide, protein, peptide, or hapten starting materials with vinylsulfone, thereby minimizing self-crosslinking and polymerization. Additionally, in these processes according to the invention, the degree of crosslinking between the reaction components can be controlled.

Applicant also has developed suitable methods for producing conjugates using homobifunctional divinylsulfone materials as a crosslinking agent, especially divinylsulfone. In this application, the term "divinylsulfone materials" will be used in a general sense to refer to any sulfone molecule that includes two vinyl sulfonyl or vinylsulfone groups in its structure. The term "divinylsulfone" will be used to refer to the following specific divinylsulfone material:

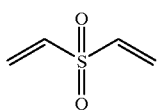

The use of divinylsulfone in the conjugation process is advantageous because it is a relatively inexpensive, stable, water soluble reagent that is readily available. As described above, other derivatization methods using divinylsulfone required a very high pH (usually 11 or more). This high pH was necessary in order to make the polysaccharide hydroxyls sufficiently nucleophilic to induce a reaction with the divinylsulfone. By contrast, in the method according to this invention, a high pH is not necessary to induce the derivatization of the polysaccharide with divinylsulfone.

In the following general description of the processes of the invention, and indeed throughout the application, the term "protein" often is used for brevity and simplicity. Those skilled in the art will recognize that proteins, peptides, or haptens can be used in the reaction processes without departing from the invention.

In the process of the invention, the polysaccharide material is first functionalized with one or more "X" groups that are more nucleophilic than the endogenous groups (e.g., the hydroxyl groups) on the polysaccharide. This X group may be, for example, an amine group, a thiol group, or a hydrazide group. After the polysaccharide is functionalized with an appropriate, limited number of the X group(s), a divinylsulfone material is added at a high concentration (i.e., in large excess), and the pH of the solution is adjusted to a range appropriate to facilitate reaction between the divinylsulfone material and the X group, but less than the pKa of the polysaccharide hydroxyls. The reaction proceeds between the divinylsulfone material and the X groups at this low pH, but substantially no reaction is induced between the divinylsulfone material and the endogenous groups on the polysaccharide (e.g., other hydroxyl groups). This allows for selective and limited derivatization of the polysaccharide material with the divinylsulfone material. The high concentration of divinylsulfone material forces the reaction to proceed and minimizes crosslinking via the X group. The divinylsulfone derivatized polysaccharides ("Ps-Vs") that are produced by this process are very stable, and can be lyophilized ("freeze-dried") and stored frozen for later use.

After the Ps-Vs material has been produced, it is then reacted with a protein component to produce the conjugate. The protein can be directly coupled to the polysaccharide by its own amines or thiols, or it may be derivatized with "Y" groups prior to conjugation. The use of Y groups may be appropriate, for example, in the following situations: (a) where it is desired to limit the number of crosslinks between the protein and the polysaccharide; or (b) where it is desired that the conjugation reaction proceed at a lower pH. Suitable Y groups include thiols or hydrazides.

In another alternative process according to the invention, the protein rather than the polysaccharide is derivatized with the divinylsulfone material. First, the protein is functionalized with an appropriate, limited number of Y groups, such as thiols or hydrazides, that are more nucleophilic than the endogenous groups (e.g., amines) on the protein. Thereafter, a large excess of the divinylsulfone material is added to the functionalized protein to produce a protein derivatized with divinylsulfone ("Protein-Vs"). The reaction proceeds between the divinylsulfone material and the Y groups at a low pH that does not substantially induce reaction between the divinylsulfone material and other endogenous groups (e.g., the amine groups) on the protein. In this manner, selective and limited derivatization of the protein with the divinylsulfone material is accomplished. After the Protein-Vs is produced, it is coupled to the polysaccharide molecule to produce the conjugate. To facilitate the conjugation reaction process, prior to conjugation, the polysaccharide can be derivatized with X groups (e.g., thiols, hydrazides, amines, or other nucleophiles).

The invention further relates to conjugate vaccines and other valuable immunological reagents that can be prepared using the conjugates produced from the processes described above.

In the processes described above, the vinylsulfone group in the Ps-Vs and Protein-Vs materials is very stable. Thus, the conjugation reaction may continue over a long time period. Additionally, the bond formed between the vinylsulfone and the thiols, amines, and hydrazides also is stable. The multiple crosslinks formed between the protein and polysaccharide improve the stability of the conjugate product. This high stability improves the yield of the conjugate product. In contrast, other crosslinking agents tend to include reactive groups that hydrolyze during the conjugation reaction process (e.g., maleimides), thereby reducing the yield of the conjugate. A further advantage that derives from this stability is that the conjugation reaction may be more homogenous because it is relatively slow, allowing for more complete mixing.

Progress of the conjugation reaction can be conveniently monitored by size exclusion high performance liquid chromatography ("HPLC"), because the vinylsulfone group contributes little to absorbance at 280 nm (this is the wavelength commonly used to monitor proteins). Remaining reactive vinylsulfone groups can be quenched by adding a small nucleophile, such as mercaptoethanol, glycine, ethanolamine, etc. Furthermore, the degree of derivatization of the polysaccharide or protein component with the vinylsulfone reagent can be conveniently determined indirectly by assaying the material with mercaptoethanol, or directly by reacting the material with a thiol reagent, such as thiol fluorescein (e.g., SAMSA Assay (from Molecular Probes of Eugene, Oreg.)).

Accordingly, the use of a divinylsulfone spacer material in the processes of the invention provides many advantages. Several of these advantages are briefly outline below:

The reagents are relatively inexpensive and water soluble

It is simple to monitor the extent of the derivatization of the polysaccharide

The two step derivatization method allows for controlled and limited derivatization Coupling selectivity and reaction rates may be controlled via pH control The reagent couples to most common nucleophiles (e.g., amines, thiols, hydrazides, hydroxyls, etc.)

Homogeneous products are produced because the reaction does not commence until the pH is appropriate Vinylsulfone contributes very little to absorbance at 280 nm, so it is easy to monitor reaction progress by HPLC Unreacted groups can be quenched easily The bonds formed are stable at neutral pH, and multipoint attachment enhances stability at higher pH The vinylsulfone group is stable, allowing activated polysaccharides to be stored Vinylsulfone it is a relatively small epitope Direct coupling with protein allows for recovery of unconjugated protein.

BRIEF DESCRIPTION OF THE DRAWINGS

The advantageous aspects of the invention will be more fully understood when considered in conjunction with the following detailed description and the attached figures wherein:

FIGS. 1(a) to 1(c) schematically illustrate general reaction schemes for the process according to the invention wherein the polysaccharide is derivatized with a homobifunctional divinylsulfone material;

FIGS. 4(a) to 4(d) are high performance liquid chromatographs that illustrate the results of Example II;

FIGS. 7(a) to 7(d) schematically illustrate the general reaction scheme for a process according to the invention wherein the polysaccharide is derivatized with a heterobifunctional vinylsulfone material;

FIGS. 8(a) to 8(c) schematically illustrate the general reaction scheme for a process according to the invention wherein the protein is derivatized with a homobifunctional divinylsulfone material;

DETAILED DESCRIPTION OF THE INVENTION

Figure 2:
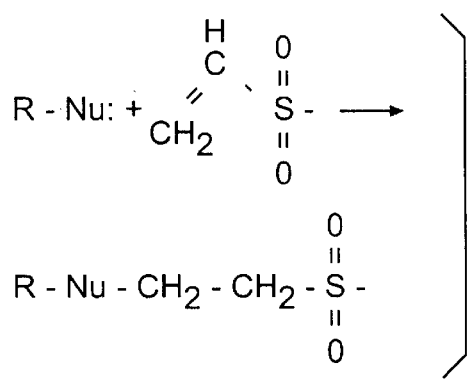
FIG. 2 illustrates the general procedure for a Michael addition reaction.

This invention relates to a process for making conjugates that are used in the preparation of vaccines and other valuable immunological reagents. As one specific example, this invention may be used to prepare a protein/polysaccharide conjugate with Vi antigen from *Salmonella typhi*.

Inducing a protein (or peptide or hapten) and a polysaccharide to couple together to form a useful immunogenic conjugate is burdened with difficulties. The materials must join together with the proper chemical structure, or the resultant material may be non-immunogenic. Proteins and polysaccharides are large, bulky molecules, and there are many possible reaction sites on each molecule. The large size and number of reaction sites increase the likelihood that the resultant conjugate will have an improper chemical structure. In addition, the large molecular size and number of reaction sites increase the availability of sites for crosslinks between the protein and polysaccharide. Excessive crosslinking can produce a thick, gelled conjugate material that is not useful in producing vaccines and immunological reagents. The crosslinking process also can destroy important epitopes, modify immunologically important sites, and add undesirable foreign epitopes.

To assist in the process for conjugating a protein and a polysaccharide, a crosslinker or a spacer can be provided on either the protein or the polysaccharide. Because the crosslinker is a smaller molecule, it helps the coupling reaction for the larger protein and polysaccharide molecules proceed more quickly by allowing better access to the large molecules, and thereby enhancing the reactivity. Additionally, the use of a crosslinker allows one to more effectively control the degree of crosslinking and the chemical structure of the resultant conjugate.

As described above, various procedures and chemistries are available for activating and attaching spacers to proteins and to polysaccharides (e.g., using CDAP, carbodiimides, NHS esters, CNBr, and carbodiimide). Dick et al. supra. In accordance with this invention, however, it has been found that the use of vinylsulfones as the reactive group in a crosslinking agent or a spacer offers a number of surprising advantages. By using vinylsulfones, reaction selectivity can be readily controlled by controlling the pH of the reaction solution. Vinylsulfones also offer good water solubility and superior stability in water. A co-solvent, such as dimethylformamide ("DMF"), can be used to aid in solubilizing and dispersion of the reagent. The linkage between the crosslinking agent and the protein or polysaccharide molecule to which it is linked is more stable when using the vinylsulfones in accordance with the invention, particularly when there are multiple vinylsulfone links. These properties make the reaction procedure simpler and easier to handle, and improved yields are realized. Suitable vinylsulfones for use in the invention are described in more detail below.

In one process according to the invention, the polysaccharide is first functionalized with an "X" group. This X group must be more nucleophilic and/or more reactive than any endogenous group (e.g., the hydroxyl groups) on the polysaccharide. As examples, the X group can be amines, thiols, or hydrazides. To place the X group on the polysaccharides, the polysaccharides may be activated using CDAP, CNBr (e.g., for Pneumococcal type 14 ("Pn14") and PRP), carbodiimide (e.g., for Vi antigen and Neisseria PsC), etc. Methods are known in the art for making such derivatizations. See, for example, Dick, et al., supra.

After the polysaccharide is derivatized with the X group, a divinylsulfone material (which is a homobifunctional vinylsulfone) is added at a high concentration (e.g., greater than 0.1 M). The pH of the solution is adjusted to an appropriate pH for reaction, for example, 5–10, depending on the type of X group. The high concentration of the divinylsulfone material forces the reaction to proceed and minimizes crosslinking via the X group. The lower pH also assists in minimizing the crosslinking of the polysaccharide hydroxyls. The resulting material is a vinylsulfone derivatized polysaccharide ("Ps-Vs").

If necessary, unreacted X groups can be capped after the vinylsulfone derivatization process. Where amines and hydrazides are used as the X group, reaction with N-hydroxysuccinimide-acetate ("NHS-acetate") can be used to cap the excess X groups. Where thiols are used as the X group, they can be capped by iodoacetamide. Such capping reactions are commonly used in this art. The excess capping reagents can be removed by standard methods known in the art, such as by dialysis, desalting, ultrafiltration, etc.

After the Ps-Vs material has been produced, it is reacted with a protein (peptide or hapten) component to produce the conjugate. The protein component need not be derivatized prior to its reaction with Ps-Vs, e.g., the protein amines can be coupled directly to the polysaccharides. Alternatively, as an earlier step, the protein can be derivatized with "Y" groups prior to conjugation. Suitable Y groups include thiols or hydrazides. The use of these Y groups may be appropriate in situations where one was attempting to limit the number of crosslinks between the protein and the polysaccharide. Furthermore, the use of appropriate Y groups may allow the conjugation reaction to proceed faster and/or at a lower pH than would otherwise be possible.

The above basic procedure is schematically illustrated in FIGS. 1(a) to 1(c). As shown in FIG. 1(a), the polysaccharide ("Ps") is first functionalized with a limited number of "X" groups (n≧1). The number of X groups may be controlled, for instance, by controlling the amount of X reagent and/or by limiting the reaction time and/or by limiting the amount of activating reagent. The X groups may include amine groups ("—NH$_2$"), thiol groups ("—SH"), or hydrazide groups ("—C(=O)—NH—NH$_2$"). Thereafter, a homobifunctional divinylsulfone material is reacted with this functionalized polysaccharide material to produce the vinylsulfone derivatized polysaccharide. As shown in FIG. 1(b), when reacting with the divinylsulfone material in this second process step, the pH of the mixture is adjusted to an appropriate level to facilitate attachment of a vinylsulfone group to the X group (but to avoid reaction of the vinylsulfone with endogenous groups (e.g., hydroxyls) on the polysaccharide). FIG. 1(b) illustrates the possible use of divinylsulfone or other divinylsulfone materials. Excess reagents are removed. Thereafter, either an underivatized protein or a protein derivatized with Y groups is reacted with the vinylsulfone derivatized polysaccharide at an appropriate pH to facilitate this reaction (but to avoid other, undesired crosslinking reactions). See FIG. 1(c). The resulting protein/polysaccharide conjugate is shown schematically in FIG. 1(c). If the protein is functionalized with a Y group, some portion of the Y group may be included in the final conjugate (not shown in FIG. 1(c)).

As an alternative to using a homobifunctional divinylsulfone crosslinking material, a heterobifunctional vinylsulfone crosslinking material can be used in the process according to the invention. In the manner described above, first the polysaccharide is derivatized with a limited number of reactive nucleophiles, such as thiols, amines, or hydrazides. This derivatized polysaccharide is then reacted with a heterobifunctional vinylsulfone reagent to produce the vinylsulfone derivatized polysaccharide ("Ps-Vs"). Excess reagent is removed, and thereafter, the Ps-Vs material is reacted with the protein to produce the conjugate. Again, the protein may be underivatized before the conjugation reaction, or it can be derivatized with Y groups as described above.

Both homobifunctional and heterobifunctional vinylsulfone materials can be used to derivatize the polysaccharide and produce the conjugates, as described above. Various homobifunctional divinylsulfone materials can be used in accordance with the invention. One suitable material is divinylsulfone itself, having the following structure:

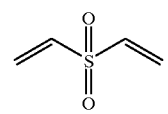

Derivatizing polysaccharides with divinylsulfone is advantageous because the vinylsulfone group is very stable at neutral pH. For this reason, the vinylsulfone derivatized polysaccharide ("Ps-Vs") can be lyophilized and stored frozen. This high stability and storability of the Ps-Vs material makes the use of divinylsulfone very advantageous as compared to the use of other crosslinking agents. The high stability of this vinylsulfone group on the polysaccharide provides another advantage. When using this stable vinylsulfone derivatized polysaccharide, the conjugation reaction may continue over a long time period. This improves the yield of the protein/polysaccharide conjugate, particularly when coupling to amines, hydrazides, or other stable groups. By contrast, other crosslinking agents tend to hydrolyze during the conjugation reaction process, thereby reducing the yield of the conjugate.

When using divinylsulfone, one should exercise caution. It should be used with appropriate safety precautions, e.g., in a hood. Furthermore, when using divinylsulfone in the derivatization reactions, the solutions should be well mixed to assure that the divinylsulfone remains dissolved. The use of a co-solvent (such as DMF) also may help assure that divinylsulfone remains in solution during the derivatization reaction.

Other suitable homobifunctional divinylsulfone materials include two sulfone groups, one at each end of the molecule, joined together by a suitable R group. The following is the general structure:

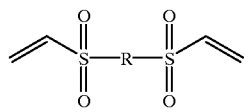

wherein R is any suitable linking group, such as a substituted or unsubstituted alkyl chain having 1 to 20 carbons. The substituent groups on the alkyl chain may include carboxyl groups. As another example, R may be polyethylene glycol.

In addition to divinylsulfone, another specific homobifunctional divinylsulfone material that can be used in the invention is 1,6-hexane-bis-vinylsulfone (molecular weight 266). This crosslinking material has the following structure:

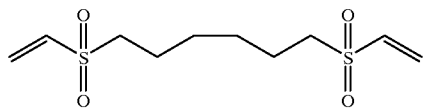

With respect to the general structure shown above, in this instance, "R" is an unsubstituted hexane group. 1,6-hexane-bis-vinylsulfone is a solid material that is less toxic and easier to handle than divinylsulfone. Additionally, 1,6-hexane-bis-vinylsulfone has reduced volatility as compared to divinylsulfone. This material is a nonvolatile, easy to work with reagent that facilitates derivatizing proteins and polysaccharides and makes it possible to incorporate a spacer into the conjugate linkage. One source of 1,6-hexane-bis-vinylsulfone is a material known as "BIOLINK™-6." BIOLINK™-6 is produced by Molecular Bio-Sciences of Huntsville, Ala.

As is evident from the structure of 1,6-hexane-bis-vinylsulfone shown above, each end of this crosslinking agent has a vinylsulfone group that may react with the protein or polysaccharide molecule during derivatization. This is a common feature of the homobifunctional divinylsulfone materials. Thus, during derivatization, particularly with long chain divinylsulfone materials (i.e., where the "R" group linking the vinylsulfone groups is rather long) each end of the divinylsulfone material can react with different portions of a single protein or polysaccharide molecule to thereby form a closed ring-like structure. This is undesirable because at least two potential crosslinking or conjugation sites on the protein or polysaccharide are rendered inactive for conjugation by the vinylsulfone ring. Additionally, because each end of homobifunctional divinylsulfone materials is reactive, two protein molecules or two polysaccharide molecules could be joined together by the divinylsulfone material during the derivatization process. This also is undesirable because it reduces the protein/polysaccharide conjugate yield. To avoid these problems, it is preferred that an excess of the homobifunctional divinylsulfone materials be used in the process according to the invention. Using an excess reduces the likelihood that each end of a single molecule of the divinylsulfone material will attach at two different locations on a single polysaccharide molecule (or a single protein molecule), especially when the polysaccharide molecule is functionalized with X-groups. It also reduces the chance that each end of a single molecule of divinylsulfone material will attach to two proteins or to two polysaccharides during the derivatization step.

As another way of avoiding these problems, a heterobifunctional vinylsulfone can be used instead of a homobifunctional vinylsulfone. Heterobifunctional vinylsulfones have a single vinylsulfone group. Thus, by selecting appropriate reaction conditions, only one end of a heterobifunctional vinylsulfone can be derivatized or attached to the polysaccharide (or protein) molecule. This fact obviates the probability of undesired bonding of each end of the vinylsulfone to a single polysaccharide or protein molecule. It also obviates the probability of two polysaccharide molecules or two protein molecules coupling together or attaching to one another during the derivatization process. Elimination of these undesired bonding scenarios increases the number of sites on the polysaccharide that are available for linking to the protein (or vice versa).

As a suitable heterobifunctional vinylsulfone material, an N-hydroxysuccinimide (NHS) vinylsulfone including an ester group having the following general structure may be used:

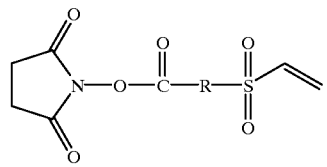

wherein R may be any suitable linking group, such as a substituted or unsubstituted alkyl chain having 1 to 20 carbon atoms. Appropriate substituent groups on the R group include carboxyls. Also, the R group may be, for example, polyethylene glycol. One specific, suitable vinylsulfone according to this general structure is as follows:

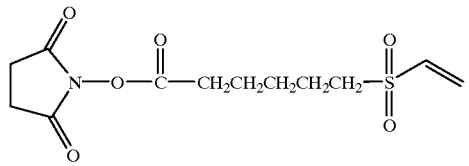

Polyethylene glycol ("PEG") based NHS-vinylsulfones of various molecular weights also can be used in the process according to the invention. Such materials are commercially available from Shearwater Polymers, Inc. (Huntsville, Ala.). One such NHS-vinylsulfone, including an ester group, has the following general structure:

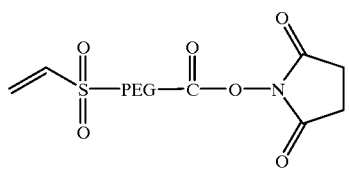

The homobifunctional and heterobifunctional vinylsulfone materials described above are derivatized onto the polysaccharide or protein molecules in order to provide a reactive site for the later protein/polysaccharide conjugation reaction. During the conjugation step, the derivatized vinylsulfone reacts with a nucleophile on the protein or polysaccharide to complete the conjugation process. Large, bulky nucleophiles typically react relatively slowly with vinylsulfones as compared to the reaction of vinylsulfones with small molecules (e.g., mercaptoethanols). See Morpurgo, et al., supra. Therefore, it was unexpected that vinylsulfones would be suitable for derivatizing high molecular weight polysaccharides, and then coupling the polysaccharides to proteins (which also are large, bulky molecules). The process according to this invention, however, illustrates that vinylsulfones are indeed suitable as spacers or crosslinking agents to couple proteins and polysaccharides for producing conjugates.

In the process of the invention, the polysaccharide is derivatized with the vinylsulfone material in one of the process steps. This derivatization provides an active reaction site on the polysaccharide. Nucleophiles, such as thiols, amines, and hydroxyls, can react with the vinylsulfones on the derivatized protein or polysaccharides by a Michael addition reaction. The general Michael addition reaction process is shown in FIG. 2. In general, thiols are reactive at a pH in the range of 6–9, amines are reactive at a pH of 7–10, and hydroxyls are reactive at pHs over 10. Michael addition reactions are described in "Michael Additions for Syntheses of Neoglycoproteins," by A. Romanowska, et al., Methods In Enzymology, Vol. 242 (1994), pp. 90–101. This Romanowska article is entirely incorporated herein by reference.

The reaction of vinylsulfone with a thiol nucleophile (e.g., wherein "Nu" is a thiol group in FIG. 2) is advantageous because it produces a stable thiol-ether linkage. In addition, this reaction proceeds with suitable kinetics over a pH range of 7–10. The vinylsulfone group is reactive with more nucleophiles than the haloacids or maleimide groups. As compared to coupling procedures using maleimides as described above, the thiol-ether formed using a vinylsulfone is a smaller epitope. Furthermore, the vinylsulfone group is much more stable than the maleimide group. As compared to the above-described processes using α-haloacids, the procedure using vinylsulfone is not light sensitive like the α-haloacid based procedure. Additionally, the vinylsulfone group is more reactive than the groups used in Romanowska.

In accordance with the invention, various different proteins can be coupled to various different polysaccharides. The following list includes examples of suitable proteins for use in accordance with the invention: viral proteins, bacterial proteins, fungal proteins, parasitic proteins, animal proteins, lipids, glycolipids, and peptides or other haptens that may be used to enhance immunological properties. Specific proteins include tetanus toxoid (TT), pertussis toxoid (PT), bovine serum albumin (BSA), lipoproteins, diptheria toxoid (DT), heat shock protein, T-cell superantigens, and bacterial outer-membrane protein. All of these protein starting materials may be obtained commercially from biochemical or pharmaceutical supply companies (e.g., American Tissue Type Collection in Rockville, Md. or Berna Laboratories of Florida) or may be prepared by standard methodologies, such as those described in J. M. Cruse and R. E. Lewis (Eds.), Conjugate Vaccines in Contributions to Microbiology and Immunology, Vol. 10 (1989). This Cruse volume is entirely incorporated herein by reference.

Examples of suitable polysaccharides for use in the process of the invention include bacterial, fungal, and viral polysaccharides. Soluble polysaccharides (i.e., polysaccharides present in solution) are preferred, and water soluble polysaccharides are particularly preferred for use in accordance with the invention. Specific examples of suitable polysaccharides include Salmonella typhi Vi antigen; Neisseria meningiditis polysaccharide C; Pneumococcal polysaccharides, such as Pneumococcal polysaccharide type 14; and dextran. A suitable listing of additional polysaccharides that may be used in accordance with this invention include the polysaccharides set forth in U.S. patent application Ser. No. 08/482,666 of Andrew Lees, filed Jun. 7, 1995 now U.S. Pat. No 5,849,301. As noted above, this application is entirely incorporated herein by reference.

Turning now to the actual process of forming the conjugates using a vinylsulfone derivatization step, various process conditions will be described. The pH of the reaction solution during the conjugation step (i.e., the step of coupling or joining the protein and the polysaccharide) is preferably in the range of 6–10. In general, it has been observed that the reaction proceeds more rapidly and completely at higher pH's in this range.

One aim of the process of the invention is to provide conjugates, such as protein/polysaccharide conjugates, that are useful in preparing vaccines or other immunologically valuable reagents. In the process of the invention, mild and limited derivatization or functionalization of the protein or the polysaccharide components using the homobifunctional or heterobifunctional vinylsulfones minimizes potential damage to immunologically important epitopes. Furthermore, the reaction conditions make it possible to separate the unreacted protein from the conjugate. This helps prevent the protein from polymerizing and provides a purer conjugate product. The coupling reaction proceeds at a reasonable speed (i.e., reasonable reaction kinetics) and at a reasonable pH. Furthermore, any remaining reagent during the conjugation step can be quenched, for example, with mercaptoethanol, ethanolamine, or glycine.

The invention will be described more specifically below in terms of various preferred embodiments and specific examples. These preferred embodiments and specific examples should be construed as being illustrative of the invention, and not as limiting the same. Additionally, certain examples use BSA as a model protein and/or dextran as a model polysaccharide. Of course, biologically relevant proteins and polysaccharides will be used in the practice of the invention. Specific examples including biologically relevant proteins and polysaccharides also are included in this application.

The following Examples also include various abbreviations, standard procedures and materials that are well known to those skilled in the art. The following information will help one to more readily understand the information included in the following examples. These definitions apply in the following examples, unless there is an indication to the contrary.

Monomeric BSA used in these examples was prepared from Cohn fraction V BSA (from Sigma Chemical Co.) by gel filtration on a 2.5×100 cm S100HR column (from Pharmacia) as described in Lees, et al., *Vaccine,* Vol. 14, No. 3 (1996) pp. 190–198. The dextran was T2000 dextran obtained from Pharmacia. Divinylsulfone was obtained from Aldrich. 1,6-hexane-bis-vinylsulfone was obtained from Molecular Biosciences of Huntsville, Ala. Tetanus toxoid, *Salmonella typhi* Vi antigen, and Neisseria PsC were obtained from SmithKline Beecham (Rixensart, Belgium). Commercial sources for suitable polysaccharides in accordance with the invention include American Tissue Type Collection of Rockville, Md. and Sigma Chemical Co.

A test for determining the presence of thiol groups used Ellman's reagent in the manner described the G. L. Ellman, *Arch. Biochem. Biophys.,* Vol. 82, pg. 70 (1959). Ellman's reagent also is known as 5,5'-dithol bis (2-nitrobenzoic acid) or "DTNB." The presence of amines was determined using a trinitrobenzenesulfonic (TNBS) acid assay, as described by J. Vidal and C. Franci, *J. Immunol. Meth.,* Vol. 86, pg. 155 (1986). The presence of hydrazides also was determined using a TNBS assay as described by Qi, et al., *Anal. Chem.,* Vol. 275, pg. 139 (1988). The presence of polysaccharides was determined using the resorcinol/sulfuric acid method of Monsigny, et al., *Anal. Chem.* Vol. 175, pg. 525 (1988), using the relevant polysaccharide standard. The presence of protein was determined using the Coomassie Plus Protein Assay Reagent (available from Pierce Chemical Co., of Rockport, Ill.) (an appropriate protein standard, such as BSA or tetanus toxoid, was used as the standard). All of these cited documents are entirely incorporated herein by reference.

"NaAc buffer," as used in this application, represents a mixture of 10 mM sodium acetate, 2 mM ethylenediamine-tetraacetate ("EDTA"), 0.1 M NaCl, and 0.02% sodium azide to provide a solution having a pH of 5. "HEPES" buffer (or "HE" buffer) represents a mixture of 0.15 M hydroxyethyl piperazine N'-2-ethane sulfonic acid ("HEPES") and 2 mM EDTA to provide a solution having a pH of 7.3. "HEPES only" or "HE only" refers to HEPES alone, without EDTA (pH=8). "5×HEPES" buffer (or "5×HE") represents a mixture of 0.75 M HEPES and 10 mM EDTA to provide a solution having a pH of 7.3. "Saline" represents a 0.15 M solution of NaCl.

When high performance liquid chromatographs ("HPLC") are conducted, a Waters model 626 pump was used with a model 600S controller and a model 486 absorbance detector. Prior to running the HPLC chromatographs, all samples were spin filtered using an ultrafree MC 0.45 μm filter unit. The HPLC column was a Phenomenex Biosep G4000 column (300×7.8 mm), equilibrated with 0.1 M potassium phosphate buffer at a pH of 7.2. The run velocity was 1 ml/min. Some runs included the use of a guard column of the same material.

In these examples, proteins were thiolated using N-succinimidyl 3-(2-pyridyldithio) propionate ("SPDP", available from BioAffinity Sciences of Rockport, Ill.) using the general protocol described in *Bioconjugate Techniques,* supra., page 230. Labeling was performed at a pH of 7.3 in HEPES buffer, followed by deprotection of the thiol at pH 5 using 50 mM dithiothreitol ("DTT"). The thiolated proteins were desalted on a gel filtration column and concentrated using a Centricon device (available from Amicon). Thiolating agents other than SPDP may be used, such as cystamine, SAMSA, Traut's reagent, mercaptoethylamine, and N-succinimidyl S-acetylthioacetate ("SATA").

Aminoethyl carboxymethyl dextran (AECM-Dex) was prepared in the manner described by Inman, *Journal of Immunology,* Vol. 114, page 704 (1975). This article also is entirely incorporated herein by reference. The high molecular weight fraction was obtained by gel filtration on an S400HR column (from Pharmacia).

EXAMPLE I

This example illustrates that a divinylsulfone material can be used to couple a protein to a polysaccharide. The coupled material (i.e., the conjugate) may be used in producing vaccines or other immunological reagents. In this example, a protein was coupled to a polysaccharide using a bis-vinylsulfone that is homobifunctional. The reaction procedure is illustrated schematically in FIGS. 3(*a*) to 3(*d*).

A. Preparation of a Thiolated Protein

In a first procedural step, a thiolated protein material (BSA-SH) was prepared. See FIG. 3(*a*). This process is described below.

1. Thiol Pyridyl Disulfide Protein

BSA was used as the model protein in this Example. Monomeric BSA was prepared by gel filtration on an S100HR column (obtainable from Pharmacia), equilibrated with saline and was concentrated by ultrafiltration to 66 mg/ml in the manner described in Lees et al., *Vaccine,* supra., 1996, Vol. 14, No. 3, pgs. 190–198. 50 μl of 5×HE buffer and 59 μl of 0.1 M SPDP (for thiolating) were added to 0.75 ml of the BSA solution (corresponding to 50 mg BSA), and the pH was maintained at 7.3. This amount of SPDP provided an eight-fold molar excess of SPDP compared to the BSA content.

2. De-protection of the Thiol

After a two hour reaction time, the thiol on the BSA material was then de-protected. 100 μl of 1 M NaAc buffer at a pH of 5 was added to 0.34 ml of the above BSA solution with mixing. Thereafter, 22 μl of 1 M DTT was added and reacted for about 20 minutes. This procedure de-protected the thiol.

3. Further Procedures

After de-protecting, the resulting material was desalted using two HiTrap columns in series (obtainable from Pharmacia), where the column was equilibrated at a pH of 5 in the NaAc buffer. Thereafter, the solution was concentrated using a Centricon 30 device obtainable from Amicon. The resultant thiolated BSA ("BSA-SH") material was found to have the following properties: (a) a BSA content of 47 mg/ml (determined by its optical density (OD) at 280 nm and an extinction coefficient of 1.5 mg/ml BSA/absorbance unit); and (b) a thiol ("SH") content of 4.6 mM SH (determined by DTNB assay). Using a weight average molecular weight of 68,000, it was determined that the resultant BSA-SH material had 6.6 SH groups/BSA.

B. Preparation of the Vinylsulfone Derivatized Polysaccharide

As a separate step in the process, a vinylsulfone derivatized dextran polysaccharide material was prepared. See FIGS. 3(*b*) and 3(*c*). The homobifunctional divinylsulfone material used in the process was a 1,6-hexane-bis-vinylsulfone material ("BIOLINK™-6," available from Molecular Bio-Sciences of Huntsville, Ala.). The dextran material first was derivatized with hydrazides using adipic dihydrazide ("ADH") and CDAP, as generally shown in FIG. 3(*b*), by the following reaction procedure. 250 μl of CDAP (at a concentration of 100 mg CDAP/ml in acetonitrile) and 250 μl of 0.2 M triethylamine were added to 10 ml of dextran (at a concentration of 10 mg/ml). After 2 minutes, 4 ml of 0.5 M ADH in HEPES only was added, and the pH of the resulting mixture was 8. This mixture was allowed to react for about one hour. It was then dialyzed, desalted, and concentrated, and the resulting hydrazide derivatized dextran product ("dextran-Hz") had a concentration of 8 mg dextran/ml in saline with a ratio of 21 hydrazides/100 kDa dextran. This procedure for producing the dextran-Hz material follows the general protocol described in the 1996 Lees article in Vaccine, supra.

1. Thiol Pyridyl Disulfide Dextran

The dextran-Hz was then derivatized with thiol pyridine. In this process, 1.5 ml of the above-mentioned dextran-Hz material (8 mg/ml) was mixed with 50 µl of 5×HE buffer at a pH of 7.3. 50 µl of 0.1 M SPDP in DMF was added for derivatizing the dextran, and the reaction proceeded for about two hours. See FIG. 3(b).

2. De-Protecting the Thiol

The thiol on the dextran was then de-protected. 200 µl of 1 M NaAc buffer at a pH of 5 was added to the dextran containing solution. Thereafter, 110 mg of DTT was added to de-protect the thiol. After a 15 minute incubation period, the resultant material was desalted on two HiTrap desalting cartridges (at pH 5) placed in series, equilibrated with the NaAc buffer.

3. Derivatization with the Divinylsulfone Material

The dextran containing tubes were pooled together to form 4 ml of the dextran material. An excess of 1,6-hexane-bis-vinylsulfone was added to derivatize the thiols as rapidly as possible. 7.6 mg of 1,6-hexane-bis-vinylsulfone in 100 µl DMF and 200 µl of 0.75 M HE buffer (pH=7.3) were added to the dextran containing pool while mixing. As noted above, the excess divinylsulfone material helps prevent undesired bonding of two polysaccharide molecules and undesired ring formation by the two reactive ends of the divinylsulfone material.

DTNB assays for the thiols confirmed that the thiols on the dextran were consumed in this reaction process. The assay results are set forth in Table 1.

TABLE 1

DTNB ASSAYS FOR THIOL*

| Time (min) | Optical Density (at 410 nm) |
|---|---|
| 0 | 0.431 |
| 5 | 0.356 |
| 10 | 0.17 |
| 15 | 0.07 |

*Assay conditions - 10 µl sample/200 µl total volume, readings taken at 410 nm.

The decreasing optical density as a function of increasing time indicates that the thiols were being reacted with (and consumed) as the reaction procedure continued.

After 20 minutes, 100 µl of 0.5 M iodoacetamide was added to the solution to cap any residual thiols. After an additional 15 minutes, the solution was concentrated with a Centricon 50 (from Amicon) to about 2 ml, and then desalted on two HiTrap columns in series, equilibrated with the NaAc buffer to a pH of about 5.

To test the completeness of the thiol de-protection, DTT was added to the dextran. No increase in the optical density at 343 nm was observed. This test confirmed that no thiols or SPDP protected thiols remained in the resulting material (i.e., de-protection was complete).

Back titration using β-mercaptoethanol ("βME") and DTNB indicated that there were about 8 vinylsulfones per 100 kDa of dextran. The resulting dex-vinylsulfone solution had 5.1 mg dextran/ml. A material having the general chemical structure illustrated in FIG. 3(c) was produced.

C. Conjugation

Figure 3A:
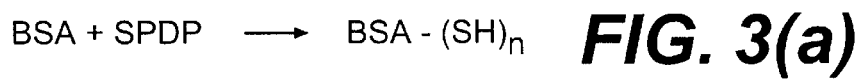
FIGS. 3(a) to 3(d) schematically illustrate the general reaction scheme for Example I in accordance with the invention.
Figure 3B:
Figure 3C:
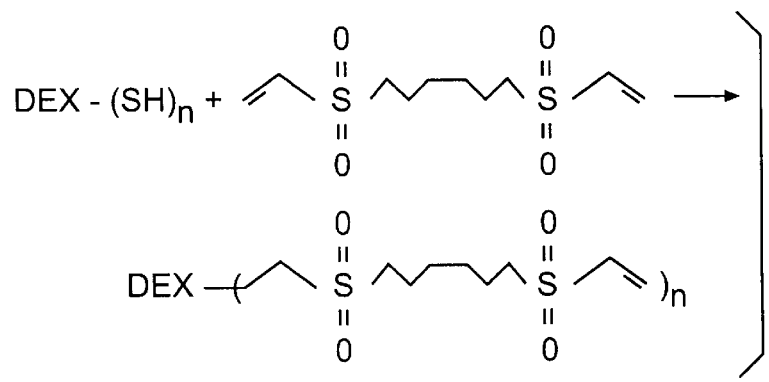
Figure 3D:
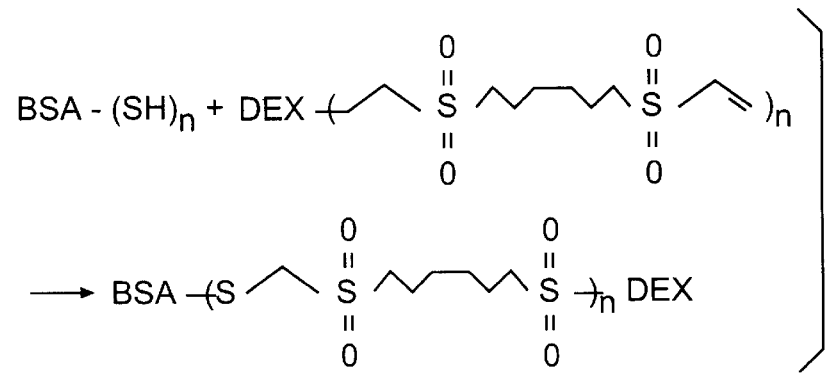

The BSA-SH thiolated protein from step A and the dex-vinylsulfone polysaccharide of step B were reacted together to form a protein/polysaccharide conjugate as generally shown in FIG. 3(d). A variety of different reaction conditions were used to test the conjugation process, as set forth in Table 2.

TABLE 2

CONJUGATION REACTION CONDITIONS

| Example No. | BSA-SH* | Dex-vinylsulf.* | Buffer |
|---|---|---|---|
| D1 | 30 µl | 275 µl | 25 µl 5X HE Buffer (pH = 7.3) |
| D2 | 30 µl | 275 µl | 25 µl 0.5 M HE only (pH = 8) |
| D3 | 30 µl | 275 µl | 25 µl 0.1 M borate (pH = 9.3) |
| D4 | 15 µl | 142 µl NaAc | 25 µl 0.1 M borate (pH = 9.3) |
| D5 | 15 µl NaAc | 142 µl | 25 µl 0.1 M borate (pH = 9.3) |

*Unless otherwise indicated. In Example Nos. D4 and D5, NaAc was added instead of the noted reactant. These Examples were conducted for background purposes.

The resultant conjugate materials were subjected to size exclusion gel filtration HPLC on a Phenomonex Biosep G4000 with a guard column. The monitored wavelength was 280 nm. The conjugate peak eluted first, corresponding to the high molecular weight (HMW) conjugate material. The area under the HPLC curves in Examples D4 and D5, in the region corresponding to the high molecular weight region of the conjugate, was used as background, and these background values were subtracted from the peak areas for each of Examples D1, D2, and D3. The total BSA amount was used to calculate the percentage of the coupled protein and polysaccharide. The results are shown in Table 3.

TABLE 3

CONJUGATION RESULTS

| Example No. | pH | % Coupled (@ 18 hr.) | % Coupled (@ 10 days) |
|---|---|---|---|
| D1 | 7.3 | 23% | 38% |
| D2 | 8 | 30% | 37% |
| D3 | 9.3 | 50.5% | 56% |

This test data illustrates that vinylsulfone derivatization and protein coupling is possible using the homobifunctional divinylsulfone material 1,6-hexane-bis-vinylsulfone as a spacer. Eighteen hours was sufficient time to couple about 50% of the protein to the polysaccharide at a pH of 9.3. In this Example, longer reaction times were needed at lower pHs.

This example also demonstrates that a homobifunctional divinylsulfone material can be used to perform a limited and controlled derivatization of the polysaccharide. This derivatized polysaccharide can be coupled to a thiolated protein to produce a protein/polysaccharide conjugate in high yield. The conjugation reaction proceeds in a relatively gentle and controlled manner.

EXAMPLE II

In accordance with the invention, divinylsulfone also can be used as the homobifunctional divinylsulfone material to activate the polysaccharide and produce the conjugates. Divinylsulfone is water soluble at high concentrations, stable, relatively inexpensive, and readily available as compared to the long chain homobifunctional and heterobifunctional vinylsulfone materials described above.

In this Example, a thiolated BSA material (BSA-SH) was coupled with a dextran polysaccharide that had been derivatized with divinylsulfone (Vs-dextran).

A. Preparation of a Thiolated BSA

In the first step, a thiolated BSA protein material (BSA-SH) was prepared by the same general procedure set forth in Example I.

1. Thiol Protecting the Protein

A commercially available BSA (from Pharmacia) was used as the model protein starting material The BSA was passed over a gel filtration column to provide a monomeric product. Starting with 400 μl of monomeric BSA solution (having a concentration of 47 mg BSA/ml), 100 μl of 5×HE buffer and 20 μl of 0.5 M iodoacetate were added to the solution, reacted for twenty minutes, and then 55 μl of 0.1 M SPDP (for thiolating) was added.

2. De-protection of the Thiol

After about one hour reaction time, the thiol on the BSA material was de-protected. The above BSA solution was mixed with a sufficient amount of 1 M NaAc buffer to adjust the pH to about 5. Thereafter, sufficient DTT was added to make the resultant solution 50 mM DTT and to de-protect the thiol.

3. Further Procedures

After de-protecting, the resulting material was desalted using two HiTrap columns in series, equilibrated to a pH of 5 with the NaAc buffer, pooled, and concentrated using a Centricon 30 device (available from Amicon). The resultant BSA-SH material was found to have the following properties: (a) a BSA content of 55.3 mg/ml (determined by its optical density (OD) at 280 nm); and (b) about 6.2 SH/BSA.

B. Preparation of the Vinylsulfone Derivatized Polysaccharide

Dextran also was used as the model polysaccharide material in this Example. First, the dextran was functionalized with an aminoethyl carboxymethyl group to produce AECM-dextran. A high molecular weight AECM-dextran fraction was obtained by gel filtration on a S400HR column (available from Pharmacia) in saline. The resultant AECM-dextran product had a concentration of 30 mg AECM-dex/ml, with a ratio of 28 amines per 100 kDa dextran.

100 μl of 1 M sodium carbonate was mixed with 1 ml of the AECM-Dex material (corresponding to 30 mg AECM-Dex). The pH of the solution was adjusted to 8 by adding HCl and/or NaOH as necessary. In a hood, 100 μl of divinylsulfone was added while mixing. The reaction proceeded overnight on a shaker. The resultant material was desalted on a 1.5×15 cm P6DG column (available from BioRad), equilibrated with saline, and then concentrated with a Centricon 50 device (available fron Amicon) to 15 mg/ml. The resultant material was vinylsulfone derivatized dextran (Dex-Vs).

C. Conjugation

The BSA-SH material was coupled to the vinylsulfone derivatized dextran at pHs of 8 and 9.3. The following Table 4 describes the various reaction conditions used in the conjugation reaction procedures of this Example (conjugate reaction time: 48 hours). Note Examples D6 and D8, where the conjugate product was BSA-S-Vs-Dex. A BSA-SH control material was produced as Example D7. This control was performed so that the HPLC chromatographs for the conjugate product could be compared against this control to assure that the observed high molecular weight peaks in Examples D6 and D8 wet not due to oxidation or self-polymerization of the thiolated protein. Likewise, a Dex-Vs control material was produced as Example D9. This control was performed so that when the chromatography was conducted for the final conjugate products, a comparison could be made to assure that the absorbance at 280 nm was not due to the vinylsulfone group or the vinylsulfone derivatized dextran.

TABLE 4

CONJUGATION REACTION CONDITIONS

| Example No. | BSA-SH | Dex-vinylsulf. | Buffer |
| --- | --- | --- | --- |
| D6 | 75 μl | 200 μl | 50 μl 0.1 M Na borate (pH = 9.3), and 10 μl 0.2 M EDTA |
| D7 (control) | 70 μl | 0 μl | 100 μl saline, 10 μl 0.2 M EDTA, and 0.25 μl 0.1 M Na borate (pH = 9.3) |
| D8 | 75 μl | 200 μl | 50 μl 0.5 M HEPES only (pH = 8) |
| D9 (control) | 0 μl | 50 μl | 37.5 μl saline and 13 μl 1. M Na carbonate (pH = 9.5) |

The HPLC chromatograph (at 280 nm) for the conjugate product prepared at a pH of 9.3 (Example D7) is shown in FIG. 4(a). The size exclusion HPLCs were performed in the manner described above. The high molecular weight peak (47%, shown at the elution time of about 6 minutes) corresponds to the conjugate product. FIG. 4(c) shows the chromatograph for Example D9, displaying a high molecular weight peak of 63%. By comparing the chromatographs for the conjugate products (FIGS. 4(a) and 4(c)) against the control products (FIGS. 4(b) and 4(d)), one can readily see that the BSA-S-Vs-Dex conjugates are produced in Examples D7 and D9, at pHs of both 8 and 9.3.

As a measure of the extent of conjugation, the weight ratio of the protein/polysaccharide in the conjugate peak is determined (e.g., mg BSA/mg Dex). The above noted HPLC device with a size exclusion column provides a percentage value for each peak, as shown in FIGS. 4(a) and 4(c), corresponding to the area under the peak with respect to the total area under the curve. The high molecular weight peak (HMW) in these figures, which elutes at a time of about 6 minutes, corresponds to the conjugate product. The protein to polysaccharide weight ratio for the conjugate is determined from the following equation:

$$\% \; HMW \; \text{peak} \times \text{mg total protein in conjugation reaction}/100 \times \text{mg total polysaccharide in conjugation reaction} = \text{mg protein/mg polysaccharide}$$

The % HMW value may be corrected for background by subtracting away any area present as a result of background measurements. Typically, however, this background level is sufficiently small as compared to the amount of the conjugate that it can be ignored for the purposes of this calculation.

Based on the information shown in FIG. 4(a), the conjugate material produced at a pH of 9.3 was found to have about 0.61 mg BSA/mg dextran. The conjugate product from the reaction at pH 8, as shown in FIG. 4(c), had about 0.83 mg BSA/mg dextran.

Accordingly, this Example demonstrates that divinylsulfone can be used to produce a protein/polysaccharide conjugate, at a high yield, in a conjugation reaction process at a pH below 10. As in Example I, Example II also demonstrates that a homobifunctional divinylsulfone material, namely divinylsulfone, can be used to perform a limited and controlled derivatization of the polysaccharide. This derivatized polysaccharide can be coupled to a thiolated protein to produce a protein/polysaccharide conjugate in high yield. The conjugation reaction proceeds in a relatively gentle and controlled manner.

EXAMPLE III

In this Example, underivatized BSA was coupled directly to a dextran polysaccharide that had been derivatized with divinylsulfone (Dex-Vs). Although Applicant does not wish to be bound by any particular theory of operation, it is believed that this coupling takes place via amines that are available on the protein.

The model protein used in this Example was a monomeric BSA material that was prepared in the manner generally described in Example II. This material had a concentration of 66 mg BSA/ml. The Dex-Vs material used in this Example was prepared through an AECM functionalized dextran, as described above in Example II. The resulting Dex-Vs material had a concentration of 15 mg/ml.

For the conjugation reaction, 107 μl of the monomeric BSA material (corresponding to about 7 mg BSA) was mixed with 200 μl of the Dex-Vs material (corresponding to about 3 mg Dex-Vs). 43 μl saline and 50 μl 1 M sodium carbonate were added to these reactants to provide a reaction pH of about 10. The resulting product was a BSA-Vs-Dextran conjugate.

The following Table 5 illustrates the kinetics of the conjugation reaction. HPLCs were run at various times during the conjugation reaction procedure in the manner described above. The peaks for the high molecular weight fraction, which eluted at about 6 minutes, were measured. This information was converted to the weight ratio of BSA to dextran in the manner described above.

TABLE 5

| Conjugation Rxn Time | Percentage of Peak (%) | mg BSA/mg Dex |
|---|---|---|
| 2 hours | 15% | 0.35 mg/mg |
| 4 hours | 20% | 0.47 mg/mg |
| 18 hours | 24% | 0.56 mg/mg |
| 3 days | 27.9% | 0.65 mg/mg |

This Example illustrates that divinylsulfone can be used to produce a derivatized polysaccharide material that will couple directly to BSA. The kinetics of the coupling, i.e., the increased coupling as a function of reaction time, is shown in Table 5.

EXAMPLE IV

Instead of derivatizing a protein with thiol nucleophiles, as used above in Example II, in this Example the protein was derivatized with hydrazides. The hydrazide nucleophile has a lower pKa than the thiol nucleophile or an amine nucleophile. This Example illustrates that, when using the hydrazide nucleophile having a low pKa, it is possible to achieve coupling or conjugation under essentially neutral pH conditions. Although hydrazide (having a pKa of approx. 2) is a weaker nucleophile than thiol or amine, it will not be protonated at neutral pH. Lower pHs also may be used.

In this Example, a hydrazide derivatized protein (BSA-Hz) was coupled to a divinylsulfone derivatized polysaccharide material (Dex-Vs). The Dex-Vs material was prepared in the manner described above in Example II. Monomeric BSA (obtained in the manner described above in Example II) was derivatized using carbodiimide and adipic dihydrazide (ADH) in the following manner. 0.2 grams of BSA (available from Intergen as endotoxin-reduced BSA) having a concentration of 20 mg/ml in saline was used as the starting solution. This material was made 0.25 M ADH by adding stock ADH solution. The pH of this mixture was adjusted to 5.1 ml of (1-(3-dimethylaminopropyl) 3-ethyl carbodiimide hydrochloride ("EDC"), having a concentration of 100 mg EDC/ml in water, was added to this solution. The reaction was allowed to proceed for 6 hours. After reaction, monomeric BSA was obtained by gel filtration by passing the reaction solution through an S100HR (2.6×97 cm) column (from Pharmacia), equilibrated with saline, and then concentrated to 22.6 mg BSA/ml. It was determined that the resultant BSA-Hz material had about 19 Hz/BSA.

200 μl of Dex-Vs (at a concentration of 15 mg/ml, corresponding to 3 mg Dex-Vs) was mixed with 310 μl BSA-Hz having a concentration of 22.6 mg/ml (corresponding to 7 mg BSA-Hz) and 100 μl 1.5 M HEPES. The corresponding reaction pH was 7.3. After 18 hours, the conjugate product was recovered. Based on size exclusion HPLC, the resulting conjugate peak, which eluted at about 6 minutes, was found to have 0.58 mg BSA-Hz/mg dextran.

Accordingly, in view of this Example, using a hydrazide derivatized protein, a protein/polysaccharide conjugate product was produced under essentially neutral pH conditions using a divinylsulfone spacer. Applicant has found that the use of lower pHs also is possible.

EXAMPLE V

A tetanus toxoid was used as the protein material in this Example to prepare a clinically relevant protein/polysaccharide conjugate. The polysaccharide in this Example was a *Salmonella typhi* Vi polysaccharide antigen that had been derivatized with divinylsulfone. Both the tetanus toxoid and the *Salmonella typhi* Vi polysaccharide antigen were obtained from SmithKline Beecham.

In a first step, the Vi antigen was derivatized with amines using ethylenediamine and carbodiimide to produce Vi-NH$_2$. This was accomplished through the following procedure.

500 μl of 1 M 2-(N-Morpholino) ethanesulfonic acid ("MES") was added to 5 ml of Vi antigen having a concentration of 5 mg Vi/ml water to provide a solution having a pH of 5.5. 250 μl of 0.1 M Sulfo-N-hydroxysuccinirnide ("sulfo-NHS") was added to this mixture. This mixture was made 0.1 M in EDC by adding 0.5 M EDC stock solution (in water) to the mixture. After 4 hours, an additional 100 μl of EDC from the stock solution was added.

After an overnight reaction, the solution was dialyzed against saline, desalted on a P6DG column (available from BioRad), and concentrated with a Macrosep50device (available from Filtron). The Vi-NH$_2$ product had a concentration of 3.8 mg/ml with 21 NH$_2$ groups per 100 kDa Vi.

This Vi-NH$_2$ product was then derivatized with divinylsulfone. 0.78 ml of the above noted Vi-NH$_2$ product (corresponding to 3 mg Vi-NH$_2$) was mixed with 100 μl of 1 M sodium carbonate at a pH of about 10.5. Thereafter, 50 μl of divinylsulfone was added to the solution. The solution became slightly yellowish in color. A TNBS assay was performed to test for the completeness of the reaction of the amines with divinylsulfone. This assay went negative within two minutes, indicating that divinylsulfone had reacted with all of the amines.

After 1.5 hours, the pH of the solution was reduced to 5 using 500 μl of 1 M NaAc buffer. This solution was dialyzed overnight against saline, desalted on a 1.5×15 cm P6DG, equilibrated with saline, and concentrated with a Centricon 50 device (from Amicon). The resulting product was *Salmonella typhi* Vi antigen that had been derivatized with vinylsulfone (Vi-Vs). The concentration of Vi-Vs was 3.1 mg/ml.

A thiolated tetanus toxoid was prepared separate from the Vi-Vs material. 0.38 ml of tetanus toxoid having a concentration of 18.6 mg/ml (corresponding to 7 mg tetanus toxoid)

was mixed with 200 μl HEPES buffer (0.15 M) to provide a solution having a pH of 7.3. Thereafter, 41 μl 0.1 M SPDP was added (40×molar excess) for thiolating. After 1 hour, the pH was reduced to 5 using an appropriate amount of 1 M NaAc buffer. The reaction mixture was made 50 mM in DTT by adding DTT from 1 M stock solution. After two hours, the reaction mixture was desalted on a P6DG (available from Bio-Rad) in HE, and then concentrated using a Centricon 50 (from Amicon). The resulting thiolated tetanus toxoid (TT-SH) concentration was 9.8 mg/ml.

The thiolated tetanus toxoid material was conjugated with the divinylsulfone derivatized Vi antigen material. In this reaction, 0.4 ml of the Vi-Vs solution (corresponding to 1.2 mg Vi-Vs) was mixed with 125 μl of the TT-SH solution (corresponding to 1.2 mg TT-SH). Additionally, 10 μl of 0.2 M EDTA and 50 μl of 0.5 M HEPES only were added. The conjugation reaction proceeded for 18 hours at a pH of 8. Based on the HPLC chromatograph data, it was estimated that the resulting TT-SH-Vs-Vi conjugate had about 0.43 mg TT/mg Vi antigen.

Accordingly, this Example illustrates that thiolated tetanus toxoid (i.e., a tetanus toxoid derivatized with a thiol group) may be reacted with a *Salmonella typhi* antigen that has been derivatized using divinylsulfone to prepare a clinically relevant protein/polysaccharide conjugate.

EXAMPLE VI

In this Example, a clinically relevant protein/polysaccharide conjugate was prepared by direct conjugation of a tetanus toxoid to vinylsulfone derivatized Vi antigen. The tetanus protein had been toxoided, and therefore, the toxoid had relatively few free amines available for direct coupling. This treatment is commonly used and well known to those skilled in this art. Thus, this Example illustrates that derivatization of the toxoid with a thiol group prior to conjugation is not necessary in all cases.

The Vi-Vs material was prepared in the manner described above in Example V. For the conjugation reaction, 0.35 ml of Vi-Vs (corresponding to about 0.8 mg Vi-Vs) was mixed with 110 μl tetanus toxoid having a concentration of 18.6 mg/ml (corresponding to 2 mg TT). 0.25 μl of 0.1 M sodium borate also was added so that the pH of the resulting solution was 9.3. The conjugation reaction proceeded at this pH.

Figure 5:
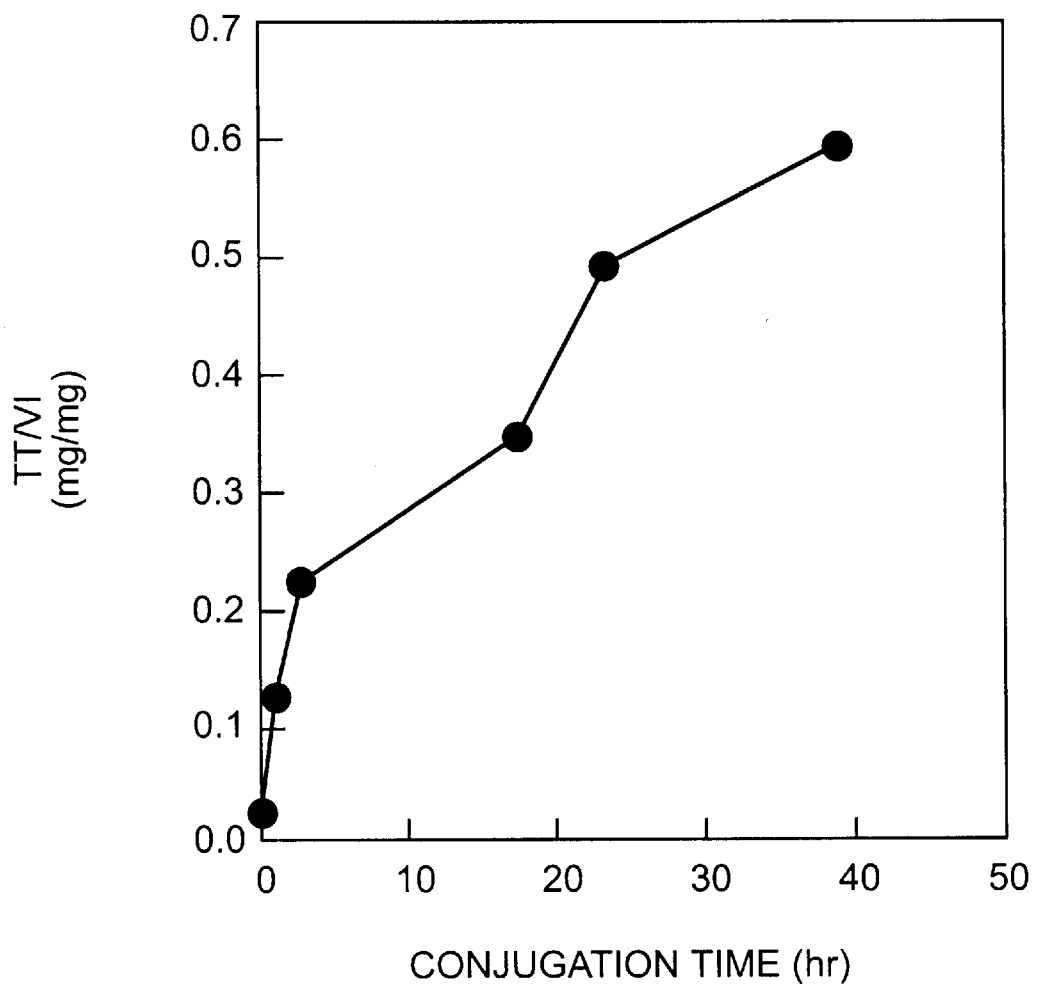
FIG. 5 is a graph showing the amount of conjugation in Example VI as a function of conjugation reaction time.

FIG. 5 illustrates the ratio of the amount of tetanus toxoid (mg TT) based on the amount of Vi antigen in the conjugate (mg Vi), as a function of conjugation reaction time (in hours). After 40 hours reaction time (pH=9.3), a ratio of about 0.6 mg TT/mg Vi was achieved. The increasing amount of conjugate product produced as a function of reaction is evident from FIG. 5.

At 40 hours, the remaining solution was passed over an S400HR column equilibrated with phosphate buffered saline. The void volume fractions corresponding to the high molecular weight fraction were pooled and sterile filtered by passing them through a 0.2 μm Millex GV filter (available from Millipor). The resulting material was assayed for protein using the Coomassie Plus Protein Assay Reagent and for polysaccharide using the resorcinol/sulfuric acid method. Through these assays, it was found that the resultant conjugate had 0.58 mg tetanus/mg Vi. Notably, this ratio obtained through the assays (0.58 mg/mg) corresponds very well with the above-noted ratio obtained from the HPLC chromatograph (0.6 mg/mg).

EXAMPLE VII

A clinically relevant protein/polysaccharide conjugate was prepared in this Example by direct conjugation of a toxoid protein to vinylsulfone derivatized Neisseria PsC. The Neisseria PsC material was obtained from SmithKline Beecham.

As a first reaction step, the Neisseria PsC material was derivatized with adipic dihydrazide (ADH). 3 ml of Neisseria PsC having a concentration of 4.8 mg/ml in water was mixed with 171 μl 0.1 M sulfo NHS (in water) and 0.5 ml of 1 M MES. The pH of the resulting solution was 5.8. Solid ADH was added to this solution until its concentration reached 0.25 M. Then, 350 μl of 0.5 M EDC was added, and the reaction proceeded for 4.5 hours at room temperature.

After reaction, the resulting mixture was dialyzed into saline, desalted on a P6DG column in saline, and concentrated with a Centricon 50 device (from Amicon) to 0.7 ml. The resulting Neisseria PsC-Hz material (i.e., the hydrazide derivatized Neisseria PsC material) had a concentration of 15.5 mg Neisseria PsC-Hz/ml. It also was determined that the derivatized Neisseria PsC material had 48 hydrazides per 100 kDa of the polysaccharide.

The hydrazide derivatized Neisseria PsC material was then derivatized with divinylsulfone. 100 μl of 0.5 M HEPES only (pH=8) and 50 μl divinylsulfone were added to 0.7 ml of the Neisseria PsC-Hz material (having a concentration of 15.5 mg/ml). After a two hour reaction time, the mixture was dialyzed overnight into saline, desalted on a P6DG column into saline, and thereafter concentrated with a Centricon 50 (Amicon) to 4 mg/ml. The resultant material was a vinylsulfone derivatized Neisseria PsC material (i.e., Neisseria PsC-Vs).

This Neisseria PsC-Vs material then was directly conjugated with a tetanus toxoid protein through the following reaction procedure. 100 μl of Neisseria PsC-Vs was mixed with 54 μl tetanus toxoid (having a concentration of 18.6 mg/ml) and 50 μl 0.1 M sodium borate. The pH of the resulting solution was 9.3. This reaction formed the TT-Vs-Neisseria PsC conjugate.

Figure 6:
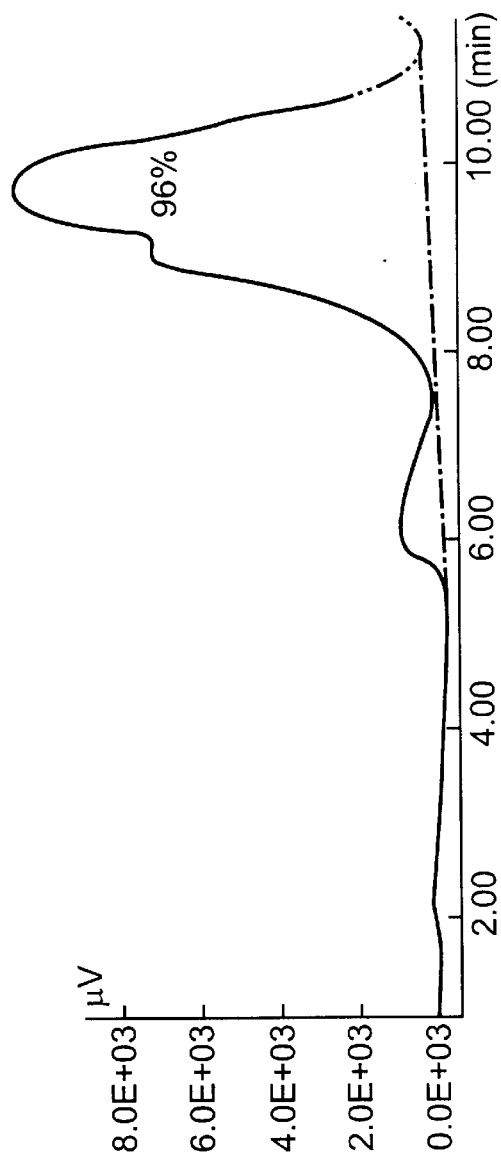
FIGS. 6(a) to 6(d) are high performance liquid chromatographs and a graph illustrating the results of Example VII.
Figure 6:
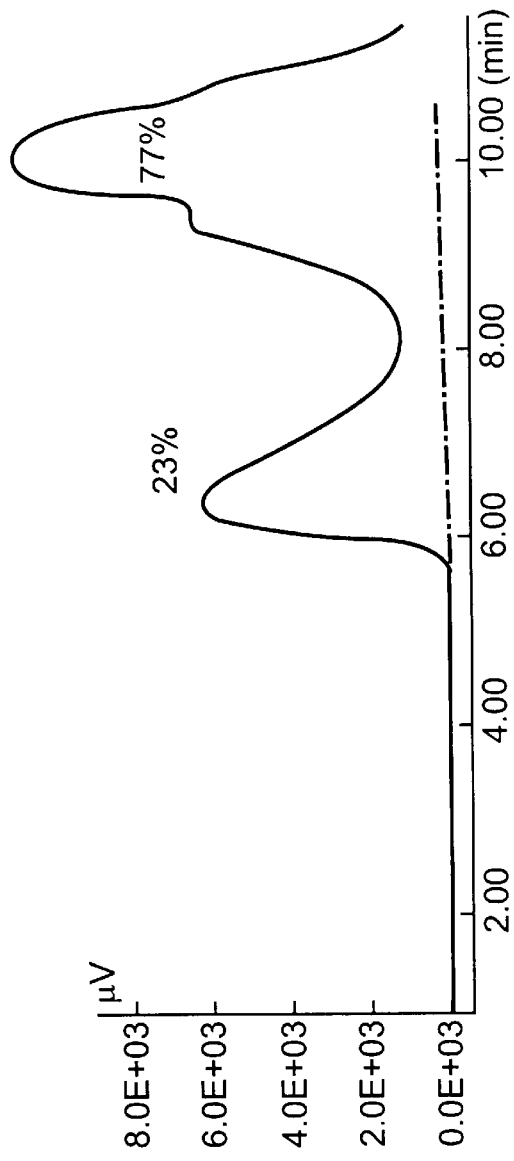
Figure 6C:
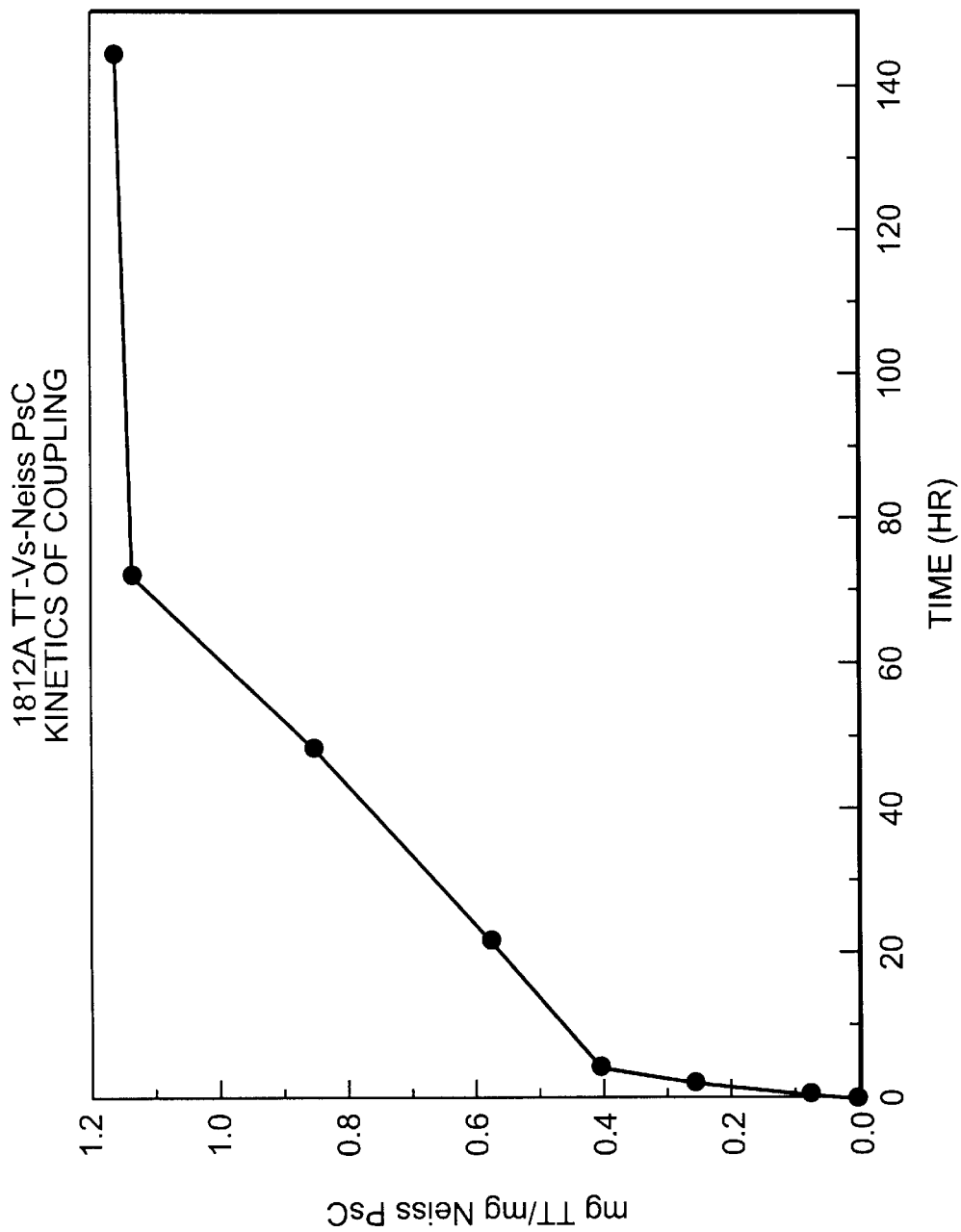
Figure 6:
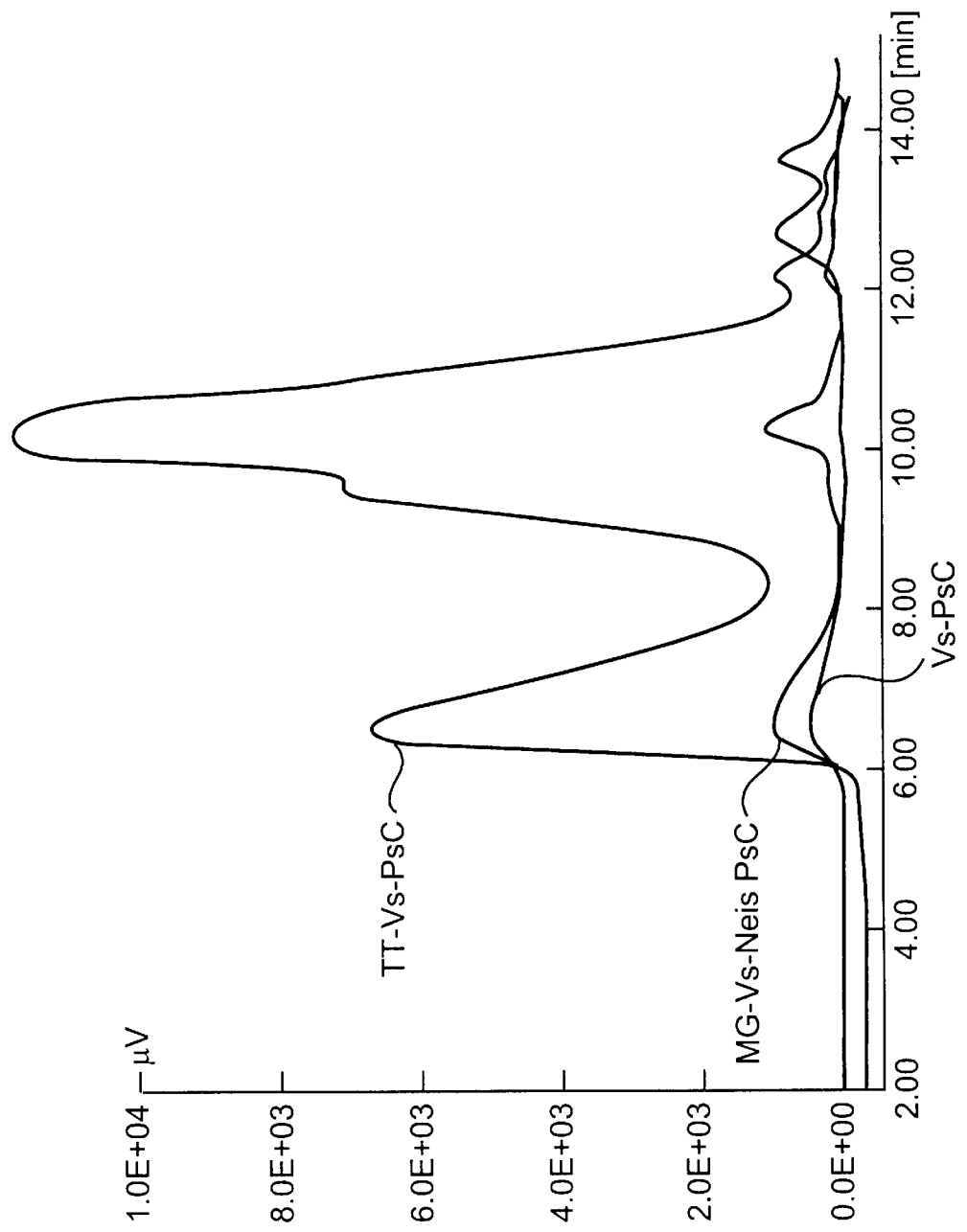

Chromatographs (HPLCs) were taken after 3 minutes and 22 hours of coupling time. FIG. 6(*a*) shows the chromatograph after 3 minutes, FIG. 6(*b*) after 22 hours. The increasing amount of the TT-Vs-Neisseria PsC conjugate is evident from the increasing size of the high molecular weight peak that elutes at about 6 minutes in the illustrated chromatographs. FIG. 6(*c*) shows the reaction kinetics for this conjugation reaction. As shown in the graph, after about 20 hours reaction time, the resulting conjugate had more than 0.5 mg TT/mg Neisseria PsC. After about 80 hours reaction time, the ratio essentially leveled off at almost 1.2 mg TT/mg Neisseria PsC.

In this Example, HPLC control samples were run to demonstrate that the high molecular weight peak was due to the formation of the TT-Vs-Neisseria PsC conjugate, and not due to the vinylsulfone group. As the controls, the Neisseria PsC-Vs material was incubated alone and with β-mercaptoethanol under the same pH and concentration conditions as used in the preparation of the conjugate. An HPLC chromatograph was run from the resultant β-mercaptoethanol-vinylsulfone-Neisseria PsC product (ME-Vs-Neisseria PsC). These control HPLCs are displayed in FIG. 6(*d*), along with the HPLC from the TT-Vs-Neisseria PsC conjugate material produced after an 18 hour reaction time. As evident from this figure, there was little absorbance at the 6 minute elution time unless the tetanus toxoid protein was present in the mixture. Thus, the vinylsulfone grouping is not the source of the absorbance in the high molecular weight peak. In addition, the tetanus did not polymerize on its own at this pH. Thus, these tests demonstrated the presence of the TT-Vs-Neisseria PsC conjugate material.

Using the general procedure described above in this Example, a separate preparation of the conjugate was produced. 215 µl of tetanus toxoid (corresponding to 4 mg TT based on a concentration of 18.6 mg TT/ml) and 50 µl of 0.1 M sodium borate were added to 0.5 ml of Neisseria PsC-Vs (2 mg) prepared in the same manner described above. The pH of the reaction solution was 9.3. The reaction proceeded for twenty-four hours to produce the conjugate.

In a manner analogous to that described above in Example VI, the conjugate solution was passed over an S400HR column equilibrated with phosphate buffered saline, and the void volume fractions corresponding to the high molecular weight fraction were obtained. Through the protein and polysaccharide assays described above, it was determined that the isolated conjugate material had 0.42 mg TT/mg Neisseria PsC.

EXAMPLE VIII

This example describes a process for coupling a protein to a polysaccharide to form a protein/polysaccharide conjugate using a heterobifunctional vinylsulfone. The general reaction procedures are illustrated in FIGS. 7(a) to 7(d).

A protein, such as monomeric BSA, is thiol protected using SPDP at a pH of 7.3. The thiol on the protein is then de-protected using 50 mM DTT at a pH of 5. The resultant material is desalted using two HiTrap columns arranged in series, equilibrated at a pH of 5. The resultant material is then concentrated. This produces a thiolated protein (Protein-SH) (see FIG. 7(a)).

In a separate step, a polysaccharide ("Ps," such as Dextran) is derivatized using hexanediamine and CDAP to produce Ps-NH$_2$ (i.e., a polysaccharide including amine derivatives) in the manner described in Lees, et al., *Vaccine*, (1996) supra. See FIG. 7(b). This Ps-NH$_2$ material is reacted with a heterobifunctional NHS-vinylsulfone at a pH of 7.3, as generally illustrated in FIG. 7(c). Examples of suitable NHS-vinylsulfones are described above, and are generally shown in FIG. 7(c). Heterobifunctional NHS-vinylsulfone materials of this general type are available from Shearwater Polymers, Inc., as also noted above.

The resultant material is desalted at a pH of 5 and concentrated to provide a Ps-vinylsulfone material having the structure shown in FIG. 7(c).

The Protein-SH and the Ps-vinylsulfone are then reacted together at a pH of 7.3. The result is a conjugated protein and polysaccharide having the general structure shown in FIG. 7(d).

EXAMPLE IX

As another alternative process, instead of derivatizing the polysaccharide with a divinylsulfone material, the protein molecule may be derivatized with the divinylsulfone material.

FIGS. 8(a) to 8(c) generally illustrate this procedure. First, the protein (e.g., BSA) is functionalized by attachment of an appropriate Y group (e.g., thiols or hydrazides). Hydrazide (Hz) is used as the Y group in FIG. 8(a). Thereafter, this functionalized protein is reacted with a divinylsulfone material (e.g., divinylsulfone), in excess, at a pH of about 5 (see FIG. 8(b)). This reaction step takes place at a relatively low pH selected such that the Y group will react with the divinylsulfone material, but the amines on the protein do not react. This produces the vinylsulfone derivatized protein material (Protein-Vs).

The Protein-Vs material is then reacted with a polysaccharide that has been previously derivatized with hydrazides (or other suitable X groups) to form the conjugate. See FIG. 8(c). In the illustrated reaction process, the polysaccharide is functionalized with an X group prior to conjugation. For this reaction process to proceed, the X group must be more nucleophilic than the endogenous protein amines (e.g., a thiol group), or it must be more reactive than the endogenous protein amines at a lower pH (e.g., a hydrazide group). The illustrated conjugation reaction step proceeds at a pH of about 5.

The general process of FIGS. 8(a) to 8(c) also could be accomplished by derivatizing the protein using a heterobifunctional vinylsulfone crosslinking agent.

EXAMPLE X

In this Example, a clinically relevant protein/polysaccharide conjugate was prepared. The polysaccharide was a Vi antigen polysaccharide that was derivatized using a heterobifunctional vinylsulfone. The protein was tetanus toxoid. The following describes the reaction procedure.

Four ml of Vi antigen polysaccharide (having a concentration of 5 mg/ml in saline) was mixed with 0.8 ml 1M 1-methylimidazole at a pH of 5. 190 mg of ADH was added, and 1 M HCl was added to adjust the pH of the solution to 5. Thereafter, 20 mg EDC was added in four portions.

The mixture was allowed to react for one hour, and then it was dialyzed into saline. The concentration of the resulting solution was 3.8 mg Vi/ml and 11 hydrazides per 100 kDa Vi antigen.

This functionalized Vi material was then thiolated. 0.9 ml of the Vi solution (having a concentration of 3.8 mg/ml) was mixed with 100 µl 1 M NaAc buffer (having a pH of 5) and 80 µl 0.1 M SPDP. After 1 hour reaction time, an additional 35 µl 0.1M SPDP was added. After 2 hours total reaction time (i.e., one hour later), an additional 35 µl 0.1M SPDP was added. After 3 total hours reaction time, DTT was added until the reaction mixture became 0.5 M in DTT. After twenty additional minutes reaction time, this mixture was desalted on a P6G cartridge, equilibrated with the NaAc buffer. It was determined that the resultant thiolated Vi antigen polysaccharide solution ("Vi-SH") was 127 µM SH, having a concentration of 0.53 mg Vi/ml and 24 SH/100 kDa Vi.

3 ml of this Vi-SH material (corresponding to 1.6 mg) were mixed with 225 µl of 0.1 M succinimidyl 4-vinylsulfonyl benzoate (which is available from Molecular Biosciences of Huntsville, Ala.). This vinylsulfone material is a heterobifunctional vinylsulfone material. Additionally, 200 µl of 5×HE buffer (pH=7.4) was added to this solution. After reacting for two hours, the resulting vinylsulfone derivatized Vi antigen ("Vi-Vs") material was desalted and concentrated with a Centricon 50 (from Amicon) to 0.8 ml.

A tetanus toxoid starting material was thiolated in a separate procedure. 312 µl of tetanus toxoid (having a concentration of 16 mg/ml and corresponding to about 5 mg TT) was mixed with 50 µl 5×HE buffer and 13 µl 0.1 M SPDP. After 1 hour, the reaction pH was reduced to 5.5 using 1 M MES. 22 µl of 1 M DTT was added, and thirty minutes later, the solution was desalted (on a P6DG column equilibrated at pH 6.8 in MES at 0.1M). This solution was then concentrated on a Centricon 50 (from Amicon) to 150 µl. The resulting material was a thiolated tetanus toxoid ("TT-SH"). The presence of the thiols was confirmed by a positive response to the addition of the DTNB reagent.

The 150 µl TT-SH was mixed with 0.8 ml of Vi-Vs prepared above and 100 µl of 0.5 M HEPES only (pH=8).

The reaction proceeded for 13 days. The void volume fractions were collected over an S400HR column (1×50 cm) in the manner described above in Example VI. From the protein assay conducted in the manner described above in Example VI, it was determined that the resulting conjugate material had 41 μg TT/ml. From the polysaccharide assay, it was determined that the conjugate had 168 μl Vi/ml. This corresponded to a weight ratio of 0.24 mg TT/mg Vi.

Thus, this Example shows that a heterobifunctional vinylsulfone may be used to derivatize the polysaccharide and produce the conjugate.

EXAMPLE XI

The following example describes the derivatization of protein and polysaccharide with heterobifunctional vinylsulfones. A Pn14 polysaccharide was derivatized with amines in the manner described in Lees, *Vaccine*, 1996, supra. The resulting Pn14-NH$_2$ material was found to have 9.9 amines per 100 kDa Pn14.

A vinylsulfone derivatized Pn14 material was made from this Pn14-NH$_2$ material in the following manner. 0.5 ml of Pn14-NH$_2$ material in saline (having a concentration of 6 mg/ml) was mixed with 100 μl 5×HE buffer (pH=7.3) and 25 μl 0.1M succinimidyl 4-vinylsulfonyl benzoate in DMF. After approximately 2 hours reaction time, the resulting vinylsulfone derivatized Pn14 material ("Pn14-Vs") was desalted on two Hitrap columns arranged in series, equilibrated with the NaAc buffer.

For another sample, the Pn14-NH$_2$ material was thiolated ("Pn14-SH"). 0.5 ml of the Pn14-NH$_2$ material (corresponding to 3 mg Pn14-NH$_2$) was mixed with 100 μl 5×HE buffer at a pH of 7.3 and 25 μl 0.1M SPDP. After two hours, the pH of the solution was reduced to 5, and then the solution was made 50 mM in DTT by adding DTT stock solution. After twenty minutes, this mixture was desalted on two Hitrap columns arranged in series, equilibrated with NaAc buffer. The resulting material was Pn14-SH.

Thiolated BSA (BSA-SH) also was made as another sample. This material was made by mixing 150 μl BSA monomer (having a concentration of 66.5 mg/ml, corresponding to 10 mg BSA) with 200 μl HE buffer (pH=7.3) and 22 μl 0.1M SPDP (corresponding to a 15×molar excess of SPDP). Reaction proceeded for two hours, and then the pH of the reaction solution was reduced to 5. The solution was then made 50 mM in DTT by adding DTT from stock solution. After twenty minutes, the resulting material was desalted on a Hitrap, equilibrated with the NaAc buffer. This material was BSA-SH.

Finally, a vinylsulfone derivatized BSA (BSA-Vs) material also was made. This material was made by mixing 150 μl of the BSA monomer (having a concentration of 66.5 mg/ml) with 200 μl HE and 22 μl 0.1M succinimidyl 4-vinylsulfonyl benzoate in DMF. After two hours, the mixture was desalted using two Hitrap columns arranged in series, equilibrated with NaAc buffer. In this manner, BSA-Vs material was prepared.

The BSA materials were concentrated on a Centricon 30 device, and the Pn14 materials were concentrated on a Centricon 50 device. The following Table shows relevant information regarding the samples.

TABLE 6

| Sample | Conc. | Thiol Content |
|---|---|---|
| Pn14-Vs | 2 mg/ml | |
| Pn14-SH | 2 mg/ml | 100 μM, 5 SH/100 kDa |
| BSA-SH | 25 mg/ml | 940 μM, 2.5 SH/BSA |
| BSA-Vs | 30 mg/ml | |

Conjugation reactions proceeded overnight at room temperature with mixing, using the ingredients from Table 6. Additionally, appropriate control samples were produced under the same reaction conditions. The following describes the various material that were prepared.

For one conjugation reaction, 240 μl Pn14-SH was mixed with 100 μl BSA-Vs and 50 μl 0.1 M sodium borate at a pH of 9.3. The resulting conjugate was BSA-Vs-SH-Pn14. The HPLC chromatograph of the conjugate is shown in FIG. 9(*a*).

For a second conjugate reaction, 400 μl Pn14-Vs was mixed with 150 μl BSA-SH and 50 μl 0.1M sodium borate at a pH of 9.3. The resulting conjugate was BSA-SH-Vs-Pn14. The HPLC chromatograph of the conjugate is shown in FIG. 9(*d*). Since the conjugate gelled, this chromatograph may not indicate the complete extent of conjugation. However, because the mixture gelled, this indicates that the conjugate was formed.

As one control, 150 μl of BSA-Vs was mixed with 50 μl 0.1 M sodium borate. The HPLC chromatograph for this control is shown in FIG. 9(*b*). As a second control, 130 μl BSA-SH was mixed with 50 μl of the 0.1M sodium borate (pH=9.3). The HPLC for this control sample is shown in FIG. 9(*c*).

Figure 9:
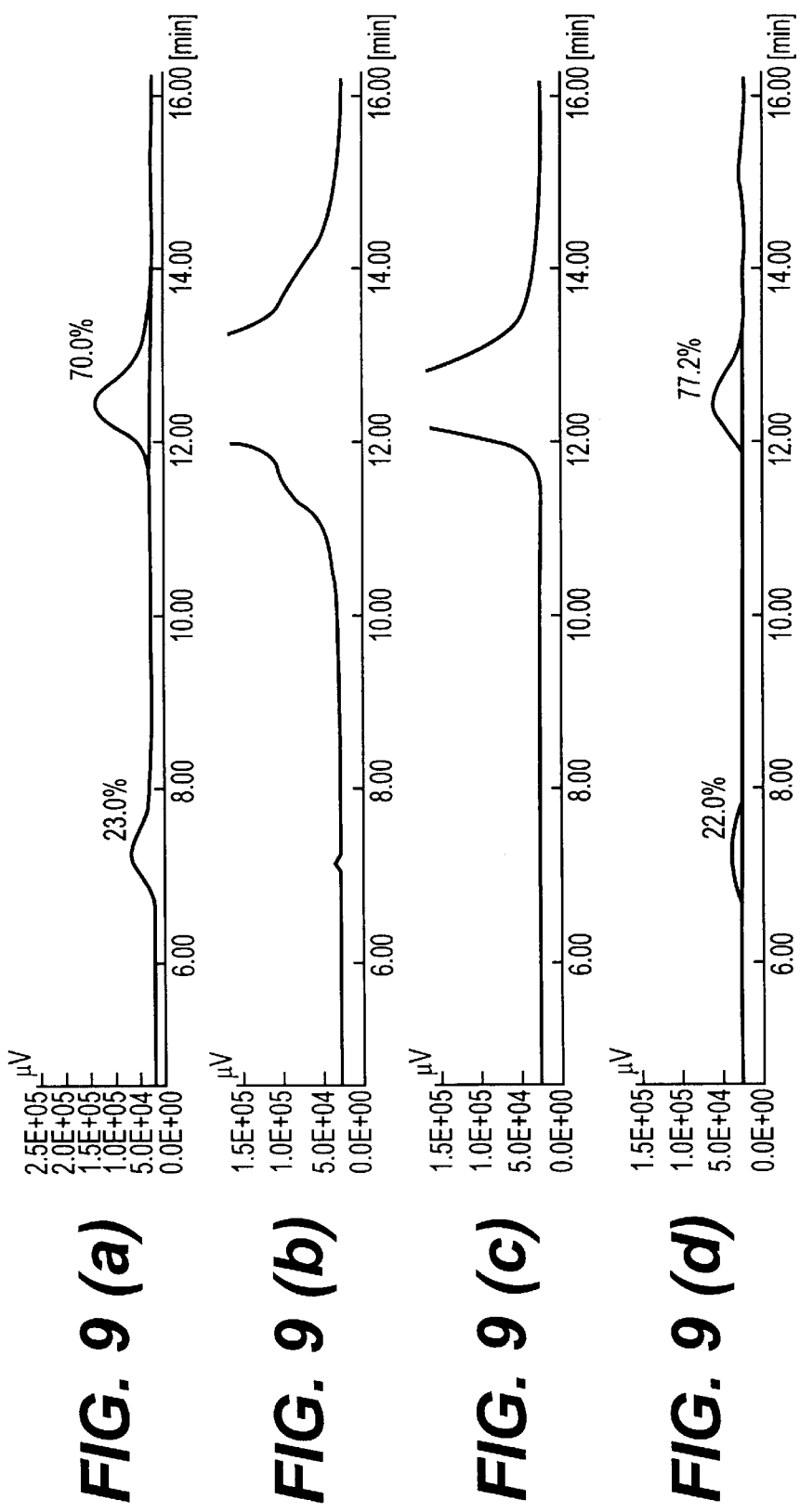
FIGS. 9(a) to 9(d) are high performance liquid chromatographs that illustrate the results of Example XI.

Both conjugate reaction solutions showed conjugate formation in the HPLCs (see FIGS. 9(*a*) and 9(*d*)), as evidenced by the high molecular weight conjugate peaks beginning at about 7 minutes elution time (22.0% and 22.8%, respectively). The controls, on the other hand, showed very little or no absorbance in the area corresponding to the conjugate peaks. The BSA-Vs control (FIG. 9(*b*)) showed a slight dimerization of the BSA-Vs.

Accordingly, these samples illustrate that a heterobifunctional vinylsulfone material can be used to derivatize a protein or a polysaccharide. The derivatized material can then be used to produce a protein/polysaccharide conjugate.

EXAMPLE XII

The following example illustrates the pH selectivity of the vinylsulfone derivatization reaction, depending on the type of nucleophile, when using divinylsulfone as the spacer.

Dextran-amine (Dex-NH$_2$) and dextran-hydrazide (Dex-Hz) were prepared according to the basic derivatization reaction procedures described in the previous examples. The Dex-NH$_2$ material had a concentration of 30 mg/ml and 28 NH$_2$/100 kDa dextran. The Dex-Hz material had a concentration 6.4 mg/ml and 16 Hz/100 kDa dextran.

The following mixtures were prepared for derivatizing these dextran materials with divinylsulfone to produce Dex-Vs:

A—0.5 ml of Dex-NH$_2$, 100 μl 0.5M HEPES only (pH=8) and 50 μl divinylsulfone;

B—0.5 ml of Dex-NH$_2$, 100 μl 1M MES (pH=6) and 50 μl divinylsulfone;

C—1 ml of Dex-Hz, 100 μl 0.5M HEPES only (pH=8) and 100 μl divinylsulfone; and

D—1 ml of Dex-Hz, 100 µl 1M MES (pH=6) and 100 µl divinylsulfone.

In each instance, the reaction proceeded overnight. After reaction, the materials were desalted on a P6DG column (1.5×10 cm), equilibrated with saline. The dextran concentration in each resultant solution was found to be about 1.3 mg dex/ml solution.

A thiolated BSA material (BSA-SH) was prepared in a separate reaction procedure. 376 µl BSA monomer having a concentration of about 66.5 mg/ml was mixed with 600 µl HE buffer and 92 µl 0.2M SPDP. After 1 hour, the pH was reduced to 5 using 300 µl 1 M NaAc buffer. 10 mg of DTT was added. 1 hour later, the mixture was desalted on a P6DG column (1.5×10 cm), equilibrated with saline. The resulting BSA-SH material was pooled, and it was determined that the solution had a concentration of 3.8 mg BSA/ml and was 1.35 mM SH. This corresponds to 24 SH groups/BSA.

1 mg of each Dex-Vs material produced above was separately mixed with 660 µl of the BSA-SH (corresponding to 2.5 mg BSA-SH), 100 µl 0.5 M HE only (pH=8) and 10 µl 0.2 M EDTA. After three days reaction time, the resultant reaction mixtures were subjected to HPLC. The following Table 7 summarizes the results of the conjugation reaction procedures:

TABLE 7

| Starting Dex Material | Activation pH | Conjugate mg BSA/mg Dex |
|---|---|---|
| A-Dex-NH$_2$ | pH = 8 | 0.56 mg/mg |
| B-Dex-NH$_2$ | pH = 6 | 0.06 mg/mg |
| C-Dex-Hz | pH = 8 | 0.4 mg/mg |
| D-Dex-Hz | pH = 6 | 0.36 mg/mg |

This data illustrates that Dex-Hz was functionalized with vinylsulfones equally well at either a pH of 8 or 6. Suitable conjugate products were obtained using the Dex-Hz based Dex-Vs materials (see C and D from Table 7). Dex-NH$_2$, on the other hand, was functionalized only at a pH of 8. A suitable conjugate was formed from dextran A (prepared at pH 8), but not from dextran B (prepared at pH 6). This data is consistent with the pKa of amines and hydrazides. Thus, as illustrated in this data, derivatization using divinylsulfone is dependent on the nucleophile present on the molecule to be derivatized and the pH of the derivatization reaction.

Direct Derivatization of Polysaccharides and Proteins

Polysaccharides can be derivatized with pendant vinylsulfones, and these derivatized polysaccharides can be coupled to derivatized or underivatized proteins. Similarly, proteins may be derivatized with pendant vinylsulfones and coupled to derivatized or underivatized polysaccharides. The direct derivatization of the protein or polysaccharide can take place under relatively mild conditions. Direct coupling using pendant vinylsulfones is advantageous because it allows the recovery of unused and/or unreacted protein or polysaccharide starting materials.

EXAMPLE XIII

This Example illustrates that the polysaccharide material may be directly derivatized with a pendant vinylsulfone material under mild reaction conditions. This derivatized polysaccharide material is then directly coupled to a protein.

In this process, dextran is used as the model polysaccharide and BSA is used as the model protein. 0.5 ml of dextran (having a concentration of 12 mg/ml) in saline was mixed with 100 µl sodium carbonate at a pH of 10.3. 50 µl of divinylsulfone was added to the solution while vortexing. The solution turned pink/brown in color. After 1 hour reaction time, the pH was reduced to about 5 by the addition of 750 µl 1 M NaAc buffer (pH of 5). This solution was desalted on two Hitrap columns connected in series, equilibrated with saline. It was determined that the concentration of the vinylsulfone derivatized dextran material (Dex-Vs) was 2.2 mg/ml.

For the conjugation reaction, 0.5 ml of the Dex-Vs material was mixed with 30 µl BSA monomer (having a concentration of 66.5 mg/ml in saline). 50 µl of 0.1 M sodium borate was added, and the pH of the resulting solution was 9.3.

As a control material, 30 µl of saline was substituted for the BSA in the conjugation reaction described above.

Figure 10:
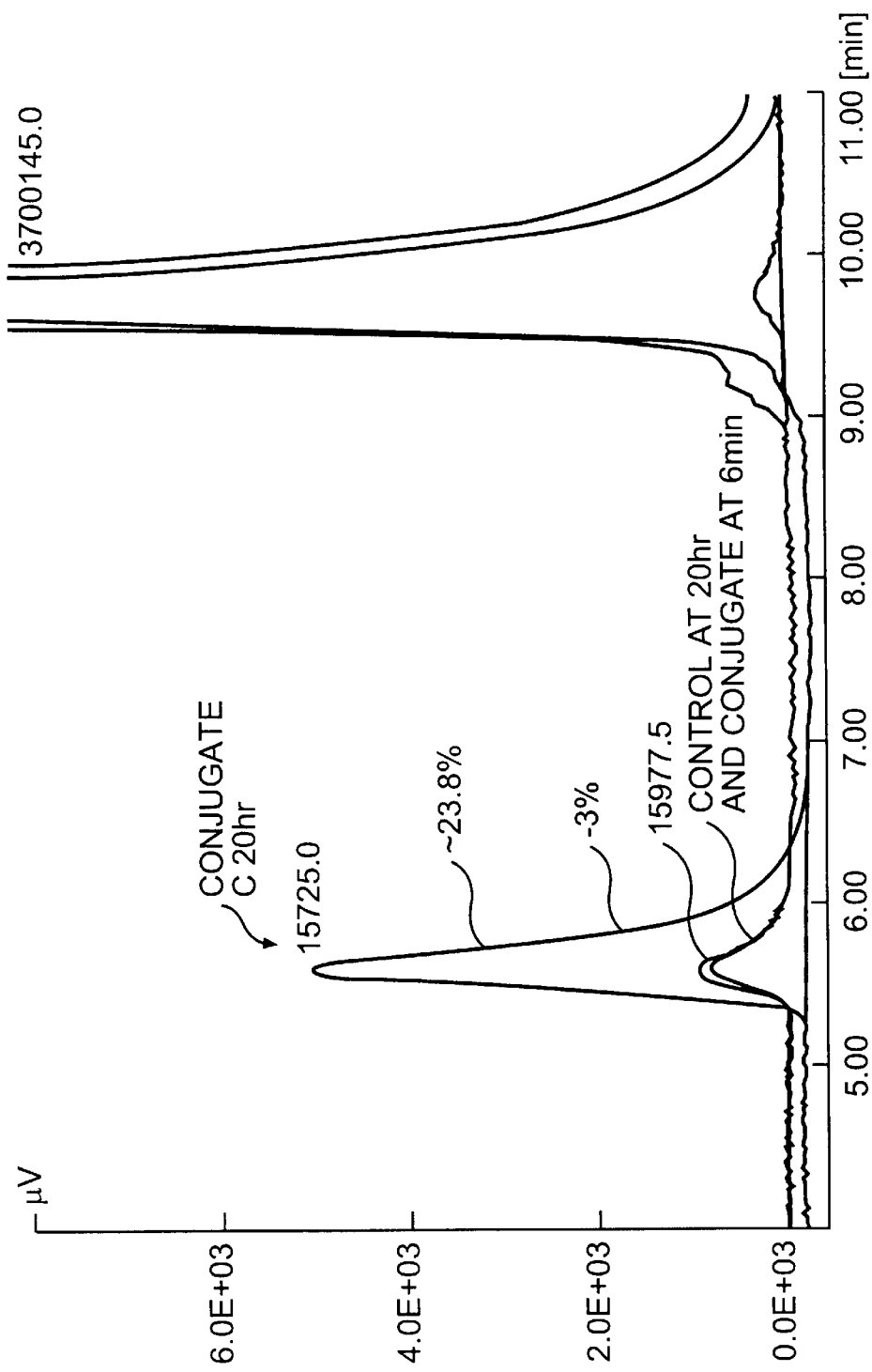
FIGS. 10(a) and (b) are a chromatograph and a graph, respectively, relating to Example XIII.
Figure 10:
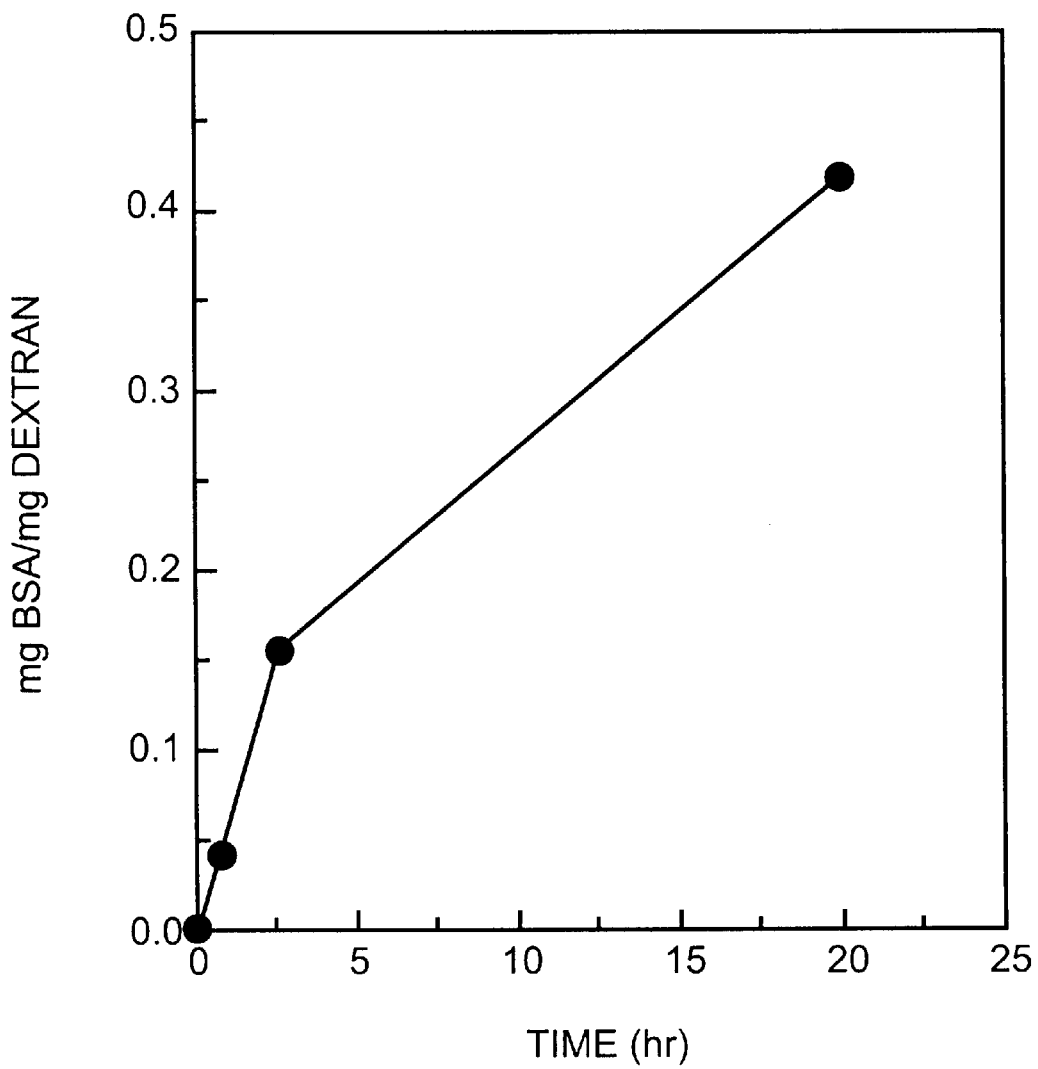

The conjugation reaction and the control mixture were monitored by HPLC. After 20 hours, a ratio of about 0.43 mg BSA/mg dextran was obtained (using the % of the HMW peak area, corrected using the control peak area). The HPLC is shown in FIG. 10(a). At twenty hours, the conjugate product had a peak of about 23.8%, and the control solution had a peak corresponding to about 3%. The control showed no increase in the small amount of absorption in the high molecular weight peak.

FIG. 10(b) illustrates the general kinetics of this conjugation reaction. The increasing ratio of mg BSA/mg dex is evident from this figure.

This Example shows that through gentle reaction conditions, a soluble polysaccharide can be functionalized directly with divinylsulfone and used to directly couple proteins.

EXAMPLE XIV

Immunogenicity data from certain clinically relevant conjugates was obtained. For the conjugate of Example VII, groups of five Balb/c mice were immunized subcutaneously with 2.5 µg of Neisseria PsC, either alone (as a control sample) or as a conjugate. The mice were boosted with the same antigen in the same amount on day 14 and bled 14 days later. Sera were assayed for anti-PsC IgG antibodies by ELISA with a cutoff of 0.1 OD. The biological activity of the antisera (i.e., its ability to protect) was determined using a bactericidal assay. The following test results were obtained:

TABLE 8

| Conjugate | Anti-PsC Titer | Bactericidal titer* |
|---|---|---|
| Example VII | 2237 | 1:40 |
| PsC alone | 6 | less than 1:10 |

*Performed as described by Wong, K.H., et al., Journal of Biological Standards, Vol. 5 (1977), beginning at page 197, which article is entirely incorporated herein by reference.

From this data, it is evident that the conjugate produced in Example VII provided a good antibody response, including a highly functional antibody response which was bactericidal, e.g., protective.

EXAMPLE XV

The immunogenicity of the conjugates of Examples V and VI also was determined. Groups of five Balb/C mice were immunized subcutaneously with the indicated amounts of Vi, either alone (as a control sample) or as a conjugate. The mice were boosted with the same antigen in the same amount of day 14 and bled 14 days later. Sera were assayed for anti-Vi IgG antibodies by ELISA with a cutoff of 0. OD. The following test results were obtained:

TABLE 9

| Conjugate | Dose Vi | Titer |
|---|---|---|
| Example V | 2.5 μg | 1092 |
| | 0.25 μg | 5300 |
| Example VI | 2.5 μg | 8020 |
| | 0.25 μg | 5029 |
| Vi | 2.5 μg | 31 |
| | 0.5 μg | 106 |

As is evident from this data, the conjugates produced in accordance with the invention produced good anti-Vi responses, at both dosages.

Information Regarding Conjugate Vaccines and Immunological Reagents

This invention further relates to vaccines and other immunological reagents that can be prepared from the conjugates produced by the method in accordance with the invention. For example, to produce a vaccine or other immunological reagent, the conjugates produced by the method according to the invention may be combined with a pharmaceutically acceptable medium or delivery vehicle by conventional techniques known to those skilled in the art. Such vaccines or immunological reagents will contain an effective therapeutic amount of the conjugate according to the invention, together with a suitable amount of vehicle so as to provide the form for proper administration to the patient. These vaccines may include alum or other adjuvants.

Exemplary pharmaceutically acceptable media or vehicles include, for example, sterile liquids, such as water and oils, including those of petroleum, animal, vegetable or synthetic origin, such as peanut oil, soybean oil, mineral oil, sesame oil, and the like. Saline is a preferred vehicle when the pharmaceutical composition is administered intravenously. Aqueous dextrose and glycerol solutions can be employed as liquid vehicles, particularly for injectable solutions. Suitable pharmaceutical vehicles are well known in the art, such as those described in E. W. Martin, *Remington's Pharmaceutical Sciences,* which reference is entirely incorporated herein by reference.

The invention also relates to the treatment of a patient by administering an immunostimulatory amount of the vaccine. The term "patient" refers to any subject for whom the treatment may be beneficial and includes mammals, especially humans, horses, cows, pigs, sheep, deer, dogs, and cats, as well as other animals, such as chickens. An "immunostimulatory amount" refers to that amount of vaccine that is able to stimulate the immune response of the patient for prevention, amelioration, or treatment of diseases. The vaccines of the invention may be administered by any suitable route, but they preferably are administered by intravenous, intramuscular, intranasal, or subcutaneous injection.

In addition, the vaccines and immunological reagents according to the invention can be administered for any suitable purpose, such as for therapeutic, prophylactic, or diagnostic purposes.

In describing the invention, applicant has set forth certain theories in an effort to disclose how or why the invention works in the manner in which it works. These theories are set forth for informational purposes only. Applicant is not to be bound by any specific chemical or physical mechanisms or theories of operation.

While the invention has been described in terms of various preferred embodiments and specific examples, those skilled in the art will recognize that various changes and modifications can be made without departing from the spirit and scope of the invention, as defined in the appended claims.

I claim:

1. A method for producing a soluble conjugate vaccine that is capable of inducing an immune response to a polysaccharide, comprising an immunogenic conjugate and a pharmaceutically acceptable medium or delivery vehicle produced by the steps of:

(a) producing the immunogenic conjugate by derivatizing a polysaccharide with a nucleophilic group selected from thiols, amines, and hydrazides reacting the derivatized polysaccharide with a vinylsulfone group to produce a vinylsulfone derivatized polysaccharide, and reacting the vinylsulfone derivatized polysaccharide with a reactant material selected from a protein, a peptide, and a hapten, wherein said vinylsulfone derivatized polysaccharide converts to a T-cell dependent antigen upon conjugation with said reactant material; and (b) combining the immunogenic conjugate with a pharmaceutically acceptable medium or delivery vehicle to form a soluble conjugate vaccine.

2. A method according to claim 1, wherein the reactant material is a protein.

* * * * *

UNITED STATES PATENT AND TRADEMARK OFFICE
CERTIFICATE OF CORRECTION

PATENT NO. : 6,309,646 B1
DATED : October 30, 2001
INVENTOR(S) : Andrew Lees

It is certified that error appears in the above-identified patent and that said Letters Patent is hereby corrected as shown below:

<u>Column 32,</u>
Line 27, "vehicle" should read -- vehicle, --.
Line 31, "hydrazides reacting" should read -- hydrazides; reacting --.
Line 35, "from a" should read -- from the group consisting of a --.

Signed and Sealed this

Seventh Day of May, 2002

*Attest:*

*Attesting Officer*

JAMES E. ROGAN
*Director of the United States Patent and Trademark Office*